United States Patent
Frinking et al.

(10) Patent No.: US 10,433,817 B2
(45) Date of Patent: Oct. 8, 2019

(54) DETECTION OF IMMOBILIZED CONTRAST AGENT WITH DYNAMIC THRESHOLDING

(71) Applicant: Bracco Suisse SA, Plan-les-Ouates (CH)

(72) Inventors: Peter Frinking, Geneva (CH); Jean-Marc Hyvelin, Geneva (CH); Thomas Fresneau, Geneva (CH)

(73) Assignee: Bracco Suisse S.A., Manno (CH)

( * ) Notice: Subject to any disclaimer, the term of this patent is extended or adjusted under 35 U.S.C. 154(b) by 0 days.

(21) Appl. No.: 15/781,088

(22) PCT Filed: Dec. 6, 2016

(86) PCT No.: PCT/EP2016/079836
§ 371 (c)(1),
(2) Date: Jun. 1, 2018

(87) PCT Pub. No.: WO2017/097738
PCT Pub. Date: Jun. 15, 2017

(65) Prior Publication Data
US 2018/0353158 A1    Dec. 13, 2018

(30) Foreign Application Priority Data
Dec. 10, 2015 (EP) .................................... 15199217

(51) Int. Cl.
*G06K 9/00* (2006.01)
*A61B 8/08* (2006.01)
(Continued)

(52) U.S. Cl.
CPC .............. *A61B 8/5223* (2013.01); *A61B 8/06* (2013.01); *A61B 8/481* (2013.01); *A61B 8/5246* (2013.01);
(Continued)

(58) Field of Classification Search
CPC ....... A61B 8/5223; A61B 8/06; A61B 8/5246; A61B 8/481; G06T 7/136; G06T 7/0012; G06T 2207/10016; G06T 2207/10132
See application file for complete search history.

(56) References Cited

U.S. PATENT DOCUMENTS

| | | |
|---|---|---|
| 5,203,337 A | 4/1993 | Feldman |
| 5,287,273 A | 2/1994 | Kupfer et al. |

(Continued)

FOREIGN PATENT DOCUMENTS

| | | |
|---|---|---|
| CN | 1977186 A | 6/2007 |
| CN | 101128154 A | 2/2008 |

(Continued)

OTHER PUBLICATIONS

Andreas et al., "Towards a Model-Free Denoising of Underwater Optical Images", Oceans-Europe 2005, vol. 1, Jun. 20, 2005, pp. 527-532.

(Continued)

*Primary Examiner* — John B Strege
(74) *Attorney, Agent, or Firm* — Fogg & Powers LLC

(57) ABSTRACT

A solution is proposed for analyzing a body-part of a patient, the body-part having been perfused before performing the method with a contrast agent capable of circulating within the patient and of being substantially immobilized on a biological target. A corresponding method comprises providing at least one filtered image comprising a plurality of filtered values for corresponding locations of the body-part, each filtered value comprising an indication of the immobilized contrast agent at the corresponding location with a contribution of the circulating contrast agent being substantially reduced, generating a thresholded image comprising a plurality of thresholded values corresponding to the filtered (Continued)

values, the thresholded image being generated by setting each thresholded value to the corresponding filtered value or to a reset value according to a comparison of the filtered value with an amplitude threshold, providing a plurality of candidate thresholds defined by corresponding candidate values of the amplitude threshold, generating a plurality of candidate images corresponding to the candidate thresholds each one comprising a plurality of candidate values corresponding to the filtered values, each candidate image being generated by setting each candidate value to the corresponding filtered value or to the reset value according to said comparison of the filtered value with the candidate threshold, calculating a plurality of comparison values corresponding to the candidate images, the comparison value of each candidate image being calculated according to a further comparison between the candidate values in an immobilization region corresponding to a group of locations containing a significant amount of the immobilized contrast agent and the candidate values in a circulation region corresponding to at least part of the locations excluding the immobilization region, determining a peak of the comparison values, and setting the amplitude threshold according to the peak of the comparison values.

21 Claims, 10 Drawing Sheets

(51) Int. Cl.
  *A61B 8/06* (2006.01)
  *G06T 7/00* (2017.01)
  *G06T 7/136* (2017.01)
(52) U.S. Cl.
  CPC .......... *G06T 7/0012* (2013.01); *G06T 7/136* (2017.01); *G06T 2207/10016* (2013.01); *G06T 2207/10132* (2013.01)

(56) References Cited

U.S. PATENT DOCUMENTS

| | | | |
|---|---|---|---|
| 5,583,902 A | 12/1996 | Bae | |
| 5,833,613 A * | 11/1998 | Averkiou | A61B 8/06 600/440 |
| 6,216,094 B1 | 4/2001 | Fox Linton et al. | |
| 6,445,945 B1 | 9/2002 | Arsenault | |
| 6,540,680 B1 | 4/2003 | Kurosaki | |
| 6,676,606 B2 * | 1/2004 | Simpson | A61B 8/481 600/458 |
| 6,740,039 B1 * | 5/2004 | Rafter | A61B 8/463 600/439 |
| 6,879,853 B2 | 4/2005 | Meaney et al. | |
| 7,069,068 B1 | 6/2006 | Oestergaard | |
| 7,998,076 B2 * | 8/2011 | Phillips | A61B 8/481 382/128 |
| 8,409,103 B2 | 4/2013 | Grunwald et al. | |
| 8,512,249 B2 * | 8/2013 | Frinking | A61B 8/481 382/128 |
| 9,198,639 B2 * | 12/2015 | Frinking | A61B 8/481 |
| 9,307,957 B2 | 4/2016 | Frinking et al. | |
| 9,734,584 B2 | 8/2017 | Frinking | |
| 10,130,342 B2 | 11/2018 | Frinking et al. | |
| 2001/0021808 A1 | 9/2001 | Shi et al. | |
| 2003/0153823 A1 | 8/2003 | Geiser et al. | |
| 2004/0172303 A1 | 9/2004 | Declerck et al. | |
| 2007/0073146 A1 * | 3/2007 | Phillips | A61B 8/481 600/437 |
| 2007/0232909 A1 | 10/2007 | Hughes et al. | |
| 2007/0279500 A1 | 12/2007 | Castorina et al. | |
| 2007/0289500 A1 | 12/2007 | Maeta et al. | |
| 2008/0139942 A1 * | 6/2008 | Gaud | A61K 49/223 600/458 |
| 2009/0171215 A1 | 7/2009 | Kato et al. | |
| 2009/0253986 A1 * | 10/2009 | Frinking | A61B 8/481 600/431 |
| 2009/0304593 A1 * | 12/2009 | Frinking | A61B 8/481 424/9.1 |
| 2011/0015522 A1 * | 1/2011 | Arditi | A61B 8/481 600/431 |
| 2011/0188722 A1 | 8/2011 | Huang | |
| 2013/0006106 A1 | 1/2013 | O'Reilly et al. | |
| 2014/0243667 A1 | 8/2014 | Wilkening | |
| 2017/0027545 A1 | 2/2017 | Casqueiro et al. | |
| 2019/0053791 A1 | 2/2019 | Frinking et al. | |

FOREIGN PATENT DOCUMENTS

| | | |
|---|---|---|
| CN | 101160097 A | 4/2008 |
| CN | 101305399 A | 11/2008 |
| CN | 101917908 A | 12/2010 |
| CN | 102223841 A | 10/2011 |
| CN | 102460506 A | 5/2012 |
| CN | 102483847 A | 5/2012 |
| EP | 0458745 A1 | 11/1991 |
| EP | 0554213 A1 | 8/1993 |
| EP | 2189112 A1 | 5/2010 |
| JP | H08336531 A | 12/1996 |
| JP | H11164832 A | 6/1999 |
| JP | 2000506398 A | 5/2000 |
| JP | 2001178717 A | 7/2001 |
| JP | 2003325518 A | 11/2003 |
| JP | 2004195228 A | 7/2004 |
| JP | 2004529697 A | 9/2004 |
| JP | 2005095376 A | 4/2005 |
| JP | 2006325746 A | 12/2006 |
| JP | 2007090075 A | 4/2007 |
| JP | 2007536048 A | 12/2007 |
| JP | 2008073338 A | 4/2008 |
| JP | 2009028194 A | 2/2009 |
| JP | 2009100971 A | 5/2009 |
| JP | 2010158360 A | 7/2010 |
| JP | 2011507647 A | 3/2011 |
| JP | 2011140527 A | 7/2011 |
| JP | 2013503681 A | 2/2013 |
| JP | 2014161735 A | 9/2014 |
| JP | 2016025993 A | 2/2016 |
| WO | 9115244 A2 | 10/1991 |
| WO | 9115244 A3 | 10/1991 |
| WO | 9409829 A1 | 5/1994 |
| WO | 9516467 A1 | 6/1995 |
| WO | 9746159 A1 | 12/1997 |
| WO | 0101865 A1 | 1/2001 |
| WO | 2004110279 A1 | 12/2004 |
| WO | 2005116902 A2 | 12/2005 |
| WO | 2006015971 A1 | 2/2006 |
| WO | 2006018433 A1 | 2/2006 |
| WO | 2006067201 A2 | 6/2006 |
| WO | 2006090309 A2 | 8/2006 |
| WO | 2006108868 A1 | 10/2006 |
| WO | 2007054544 A1 | 5/2007 |
| WO | 2008136201 A1 | 11/2008 |
| WO | 2009083557 A1 | 7/2009 |
| WO | 2010058014 A1 | 5/2010 |
| WO | 2010142694 A1 | 12/2010 |
| WO | 2011026866 A1 | 3/2011 |
| WO | 2011110552 A1 | 9/2011 |
| WO | 2014096041 A1 | 6/2014 |

OTHER PUBLICATIONS

Canadian Intellectual Property Office, "Office Action from CA Application No. 2769164 dated May 26, 2016", from Foreign Counterpart to PCT Application No. PCT/EP2010/062816, dated May 26, 2016, pp. 1-4, Published: CA.

European Patent Office, "Communication pursuant to Article 94(3) from EP Application No. 13814107.2 dated Apr. 20, 2016", from Foreign Counterpart to PCT Application No. PCT/EP2013/077152,

(56) References Cited

OTHER PUBLICATIONS dated Apr. 20, 2016, pp. 1-5, Published: EP.
Fisher et al., "Contrast Stretching", Histogram Equalization, Internet Citation, 1994, XP002291289, retrieved from Internet: http://www.cee.hw.ac.uk/hipr/html/stretch.html.
Frinking et al., "Subharmonic Scattering of Phospholipid-Shell Microbubbles at Low Acoustic Pressure Amplitudes", IEEE Transactions on Ultrasonics, Ferroelectrics, and Frequency Control, Aug. 2010, pp. 1-10, vol. 57, Number S, IEEE.
Futterer et al., "Prostate Cancer Localization with Dynamic Contrast-enhanced MR Imaging and Proton MR Spectroscopic Imaging", Radiology, Nov. 2006, pp. 1-11, vol. 241, No. 2, RSNA.
Greis, "Technology overview: SonoVue (Bracco, Milan)", European Radiology, Nov. 2004, pp. 1-6, Springer-Verlag 2004.
International Bureau, "International Preliminary Report on Patentability from PCT Application No. PCT/EP2008/068247 dated Jun. 29, 2010", from Foreign Counterpart to EP Application No. 07124133.5, dated Jun. 29, 2010, pp. 1-7, Published: Switzerland.
International Bureau, "International Preliminary Report on Patentability from PCT Application No. PCT/EP2011/053460 dated Sep. 11, 2012", from Foreign Counterpart to EP Application No. 10155926.8, dated Sep. 11, 2012, pp. 1-8, Published: Switzerland.
International Searching Authority, "International Search Report and Written Opinion from PCT Application No. PCT/EP2010/058031 dated Nov. 29, 2010", from Foreign Counterpart to EP Application No. 09162171.4, dated Nov. 29, 2010, pp. 1-5, Published: EP.
International Searching Authority, "International Search Report and Written Opinion from PCT Application No. PCT/EP2015/097020 dated Jul. 23, 2015", from Foreign Counterpart to EP Application No. 14163716.5, dated Jul. 23, 2015, pp. 1-14, Published: WO.
International Searching Authority, "International Search Report and Written Opinion from PCT Application No. PCT/EP2016/079836 dated Feb. 2, 2017", pp. 1-16. Published in EP.
International Searching Authority, "International Search Report from PCT Application No. PCT/EP2008/068247 dated Apr. 20, 2009", from Foreign Counterpart to EP Application No. 07124133.5, dated Apr. 20, 2009, pp. 1-5, Published: WO.
International Searching Authority, "International Search Report from PCT Application No. PCT/EP2010/062816 dated Oct. 13, 2010", from Foreign Counterpart to EP Application No. 09169189.9, dated Oct. 13, 2010, pp. 1-4, Published: EP.
International Searching Authority, "International Search Report from PCT Application No. PCT/EP2011/053460 dated May 16, 2011", from Foreign Counterpart to EP Application No. 10155926.8, dated May 16, 2011, pp. 1-6, Published: WO.
International Searching Authority, "International Search Report from PCT Application No. PCT/EP2013/077152 dated Apr. 4, 2014", from Foreign Counterpart to EP Application No. 12199175.6, dated Apr. 4, 2014, pp. 1-5, Published: WO.
Japanese Patent Office, "Notification of Reasons for Refusal from JP Application No. 2012-514452 dated Jan. 7, 2014", from Foreign Counterpart to PCT Application No. PCT/EP2010/058031, dated Jan. 7, 2014, pp. 1-6, Published: JP.
Japanese Patent Office, "Office Action from JP Application No. 2010-540122 dated Nov. 26, 2014", from Foreign Counterpart to PCT Application No. PCT/EP2008/068247, dated Nov. 26, 2014, pp. 1-2, Published: JP.
Japanese Patent Office, "Office Action from JP Application No. 2016-561335 dated Nov. 2, 2018", from Foreign Counterpart to PCT Application No. PCT/EP2015/097020, dated Nov. 2, 2018, pp. 1-5, Published: JP.
Kim et al., "Wash-In Rate on the Basis of Dynamic Contrast-Enhanced MRI: Usefulness for Prostate Cancer Detection and Localization", Journal of Magnetic Resonance Imaging, 2005, pp. 1-8, Wiley-Liss, Inc.
Krix et al., "Quantification of Perfusion of Liver Tissue and Metastases Using a Multivessel Model for Replenishment Kinetics of Ultrasound Contrast Agents", Ultrasound in Medicine and Biology, 2004, pp. 1355-1363, vol. 30, No. 10, World Federation for Ultrasound in Medicine and Biology.

Lanza, et al. "Targeted Ultrasonic Contrast Agents for Molecular Imaging and Therapy", Progress in Cardiovascular Diseases, Jul./Aug. 2001, pp. 13-31, vol. 44, No. 1, W.B Saunders Company.
Linder, et al., "Albumin Microbubble Persistence During Myocardial Contrast Echocardiography Is Associated With Microvascular Endothelial Glycocalyx Damage", Circulation Journal of the American Heart Association, 1998, pp. 1-9, American Heart Association.
Linton, et al., "A new method of analysing indicator dilution curves", Cardiovascular Research, Jan. 9, 1995, pp. 1-10, Elsevier Science B.V.
Mohs, et al, "An Integrated Widefield Imaging and Spectroscopy System for Contrast-Enhanced, Image-Guided Resection of Tumors", IEEE Transactions on Biomedical Engineering, vol. 62, No. 5, May 2015; pp. 1416-1424.
Pochon, et al., "BR55: A Lipopeptide-Based VEGFR2-Targeted Ultrasound Contrast Agent for Molecular Imaging of Angiogenesis", Investigative Radiology, Feb. 2010, pp. 1-7, vol. 45, No. 2, Lippincott Williams and Wilkins.
Po-Hsiang et al., "Imaging Local Scatterer Concentrations by the Nakagami Statistical Model", Ultrasound in Medicine and Biology, New Nork, NY, US, vol. 33, No. 4, Mar. 27, 2007, pp. 608-619.
Rafter, et al., "Imaging technologies and techniques", Cardiology Clinics, 2004, pp. 181-197, Elsevier Inc.
Rognin et al., "A New Method for Enhancing Dynamic Vascular Patterns of Focal Liver Lesions in Contrast Ultrasound", IEEE Ultrasonics Symposium, 2007, pp. 546-549, IEEE.
State Intellectual Property Office, P.R. China, "Office Action from CN Application No. 201080025290.5 dated Sep. 12, 2013", from Foreign Counterpart to PCT Application No. PCT/EP2010/058031, dated Sep. 2, 2013, pp. 1-24, Published: CN.
State Intellectual Property Office, P.R. China, "Office Action from CN Application No. 201380066958.4 dated Mar. 31, 2017", from Foreign Counterpart to PCT Application No. PCT/EP2013/077152, dated Mar. 31, 2017, pp. 1-23, Published: CN.
State Intellectual Property Office, P.R. China, "Office Action from CN Application No. 201580011243.8 dated Dec. 5, 2018", dated Dec. 5, 2018, pp. 1-34, Published: CN.
Tardy, et al., "Ultrasound Molecular Imaging of VEGFR2 in a Rat Prostate Tumor Model Using BR55", Investigative Radiology, Oct. 2010, pp. 573-578, vol. 45, No. 10, Lippincott Williams and Wilkins.
U.S. Patent and Trademark Office, "Advisory Action", U.S. Appl. No. 12/811,089, dated Jan. 15, 2015, pp. 1-3, Published: US.
U.S. Patent and Trademark Office, "Advisory Action", U.S. Appl. No. 12/811,089, dated Feb. 12, 2014, pp. 1-3, Published: US.
U.S. Patent and Trademark Office, "Advisory Action", U.S. Appl. No. 13/377,143, dated Oct. 21, 2014, pp. 1-6, Published: US.
U.S. Patent and Trademark Office, "Final Office Action", U.S. Appl. No. 12/811,089, dated Oct. 28, 2013, pp. 1-22, Published: US.
U.S. Patent and Trademark Office, "Final Office Action", U.S. Appl. No. 12/811,089, dated Sep. 17, 2014, pp. 1-10, Published: US.
U.S. Patent and Trademark Office, "Final Office Action", U.S. Appl. No. 13/377,143, dated Jul. 24, 2014, pp. 1-41, Published: US.
U.S. Patent and Trademark Office, "Final Office Action", U.S. Appl. No. 13/607,354, dated Sep. 2, 2016, pp. 1-11, Published: US.
U.S. Patent and Trademark Office, "Notice of Allowability", U.S. Appl. No. 14/654,449, dated May. 18, 2017, pp. 1-6, Published: US.
U.S. Patent and Trademark Office, "Notice of Allowance", U.S. Appl. No. 12/811,089, dated Mar. 2, 2015, pp. 1-16, Published: US.
U.S. Patent and Trademark Office, "Notice of Allowance", U.S. Appl. No. 13/377,143, dated Dec. 7, 2015, pp. 1-11, Published: US.
U.S. Patent and Trademark Office, "Notice of Allowance", U.S. Appl. No. 13/393,633, dated Sep. 3, 2014, pp. 1-17, Published: US.
U.S. Patent and Trademark Office, "Notice of Allowance", U.S. Appl. No. 13/607,354, dated Jul. 12, 2018, pp. 1-9, Published: US.
U.S. Patent and Trademark Office, "Notice of Allowance", U.S. Appl. No. 14/654,449, dated Apr. 13, 2017, pp. 1-7, Published: US.
U.S. Patent and Trademark Office, "Notice of Allowance", U.S. Appl. No. 15/302,467, dated Mar. 22, 2019, pp. 1-31, Published: US.
U.S. Patent and Trademark Office, "Office Action", U.S. Appl. No. 12/811,089, dated Mar. 28, 2013, pp. 1-27, Published: US.

(56) References Cited

OTHER PUBLICATIONS

U.S. Patent and Trademark Office, "Office Action", U.S. Appl. No. 12/811,089, dated Apr. 24, 2014, pp. 1-18, Published: US.
U.S. Patent and Trademark Office, "Office Action", U.S. Appl. No. 13/377,143, dated Jan. 8, 2014, pp. 1-41, Published: US.
U.S. Patent and Trademark Office, "Office Action", U.S. Appl. No. 13/377,143, dated Aug. 14, 2015, pp. 1-9, Published: US.
U.S. Patent and Trademark Office, "Office Action", U.S. Appl. No. 13/393,633, dated Apr. 7, 2014, pp. 1-10, Published: US.
U.S. Patent and Trademark Office, "Office Action", U.S. Appl. No. 13/607,354, dated Feb. 10, 2015, pp. 1-8, Published: US.
U.S. Patent and Trademark Office, "Office Action", U.S. Appl. No. 13/607,354, dated Jul. 5, 2017, pp. 1-7, Published: US.
U.S. Patent and Trademark Office, "Office Action", U.S. Appl. No. 13/607,354, dated Aug. 31, 2015, pp. 1-11, Published: US.
U.S. Patent and Trademark Office, "Office Action", U.S. Appl. No. 13/607,354, dated Sep. 17, 2014, pp. 1-35, Published: US.
U.S. Patent and Trademark Office, "Office Action", U.S. Appl. No. 14/654,449, dated Dec. 2, 2016, pp. 1-18, Published: US.
U.S. Patent and Trademark Office, "Office Action", U.S. Appl. No. 15/302,467, dated Nov. 26, 2018, pp. 1-21, Published: US.
Wang et al., "Self-adaptive Contrast Enhancement Algorithm for Infrared Images based on Plateau Histogram", ACTA Photonica Sinica, vol. 34, No. 2, Feb. 28, 2005, China Academic Journal Electronic Publishing House, Bejing, China, http://www.cnki.net, pp. 1-3.
Zhang, et al., "A Novel Model for Contrast Enhanced Ultrasound Video and Its Applications", IEEE Ultrasonics Symposium, 2006, pp. 1726-1729, IEEE.
China National Intellectual Property Administration, "Second Office Action from CN Application No. 201580011243.8 dated Apr. 25, 2019", pp. 1-11, Published: CN.

* cited by examiner

DETECTION OF IMMOBILIZED CONTRAST AGENT WITH DYNAMIC THRESHOLDING

This application claims priority to International Patent Application No. PCT/EP2016/079836 filed on Dec. 9, 2016, which claims priority to EP Patent Application No. 15199217.9 filed on Dec. 10, 2015.

TECHNICAL FIELD

The present disclosure relates to the medical imaging field. More specifically, this disclosure relates to the detection of immobilized contrast agents.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

Medical imaging is a well-established technique (in the field of equipment for medical applications), which allows analyzing a body-part of a patient in a substantially non-invasive manner. A specific medical imaging technique is based on the administration of an ultrasound contrast agent (UCA) to the patient (for example, comprising a suspension of phospholipid-stabilized gas-filled microbubbles); the contrast agent acts as an efficient ultrasound reflector, so that it provides a corresponding enhancement in images of a body-part of the patient that are acquired by means of an ultrasound scanner.

The contrast agent may also be adapted to reach a specific (biological) target (for example, expressed in a lesion) and then to remain immobilized thereon. Particularly, in Ultra-Sound Molecular Imaging (USMI) techniques this result is achieved by using a (molecularly) targeted contrast agent that is formulated for attaching to the corresponding target (for example, by incorporating a ligand in its formulation capable of interacting with inflammatory or tumoral tissues). The detection of the targeted contrast agent that is immobilized allows identifying its target (for example, the corresponding lesion that would otherwise be difficult to discover); moreover, the quantification of this immobilized (targeted) contrast agent allows determining a condition of the target (for example, in therapeutic follow-up of the lesion).

However, the identification of the contribution of the immobilized contrast agent in the enhancement of the images, or Targeted Enhancement (TE), is hindered by the fact that only a small fraction of the targeted contrast agent actually reaches the target and remains immobilized thereon, whereas the rest of the targeted contrast agent instead continues to circulate for quite a long time (up to 10-30 min.), for example, until it is filtered out by the lungs and/or in the liver of the patient; therefore, until most of this circulating (targeted) contrast agent has disappeared, it is not possible to discriminate the immobilized contrast agent from the circulating contrast agent.

A common approach for detecting the immobilized contrast agent at an early stage after administration of the targeted contrast agent is a Differential Targeted Enhancement (dTE) technique. In this case, destructive pulses with high mechanical index (MI) are applied to the body-part so as to destroy most of the (immobilized and circulating) targeted contrast agent. Images acquired before the application of the destructive pulses (and then comprising the contribution of both the immobilized contrast agent and the circulating contrast agent) are filtered by subtracting images acquired after a short delay (of typically 30-90 s) from the application of the destructive pulses (and then mainly comprising the contribution of the circulating contrast agent only), so as to mainly preserve the contribution of the immobilized contrast only. However, in this way it is not possible to image the body-part again to detect the immobilized contrast agent since it has been destroyed by the application of the destructive pulses.

Alternatively, WO-A-2007/054544 (the entire disclosure of which is herein incorporated by reference) proposes processing the images to reduce a contribution of the circulating contrast agent by substantially suppressing (or at least attenuating) pixel values of the images showing high variations over time (at the same time preserving the pixel values showing low variations over time). For this purpose, the images are filtered by applying a modified Minimum Intensity Projection (Min_IP) algorithm, wherein each pixel value is replaced by the minimum among the pixel value itself and the corresponding pixel value in one or more preceding images.

However, a residual contribution of the circulating contrast agent may still be present in the images so filtered due to an incomplete suppression thereof. The residual contribution of the circulating contrast agent may degrade a conspicuity of the immobilized contrast agent, and then hamper the detection and especially the accurate quantification thereof.

The residual contribution of the circulating contrast agent generally has relatively low intensity. Therefore, a common approach for suppressing (or at least reducing) the residual contribution of the circulating contrast agent is thresholding the filtered images by resetting their pixel values lower than an amplitude threshold to zero; for example, in WO-A-2007/054544 the amplitude threshold is set to 0-5% of an allowable maximum of the pixel values.

However, this operation may have undesirable effects. Particularly, if the amplitude threshold is too low the thresholding of the filtered images may be ineffective in reducing the residual contribution of the circulating contrast agent (for example, in case of high gain and/or high dynamics of the ultrasound scanner or of high concentration of the targeted contrast agent); conversely, if the amplitude threshold is too high the thresholding of the filtered images may reduce the contribution of the immobilized contrast agent as well (for example, in case of low gain and/or low dynamics of the ultrasound scanner or of low concentration of the targeted contrast agent).

All of the above hinders the clinical application of medical imaging techniques based on the use of targeted contrast agents.

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure is based on the idea of setting the amplitude threshold dynamically.

Particularly, an aspect provides a method for analyzing a body-part of a patient that comprises generating a thresholded image from at least one filtered image (wherein a contribution of a circulating contrast agent has been substantially reduced) according to an amplitude threshold, wherein candidate images are generated from the filtered image according to a plurality of candidate thresholds, comparison values are calculated from the candidate images according to a comparison of their values in different regions and the amplitude threshold is set according to a peak of the comparison values.

A further aspect provides a software program for implementing the method.

A further aspect provides a software program product for implementing the method.

A further aspect provides a corresponding system.

A further aspect provides a corresponding diagnostic method.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, such as value, content and representation). Particularly.

DETAILED DESCRIPTION

Figure 1:
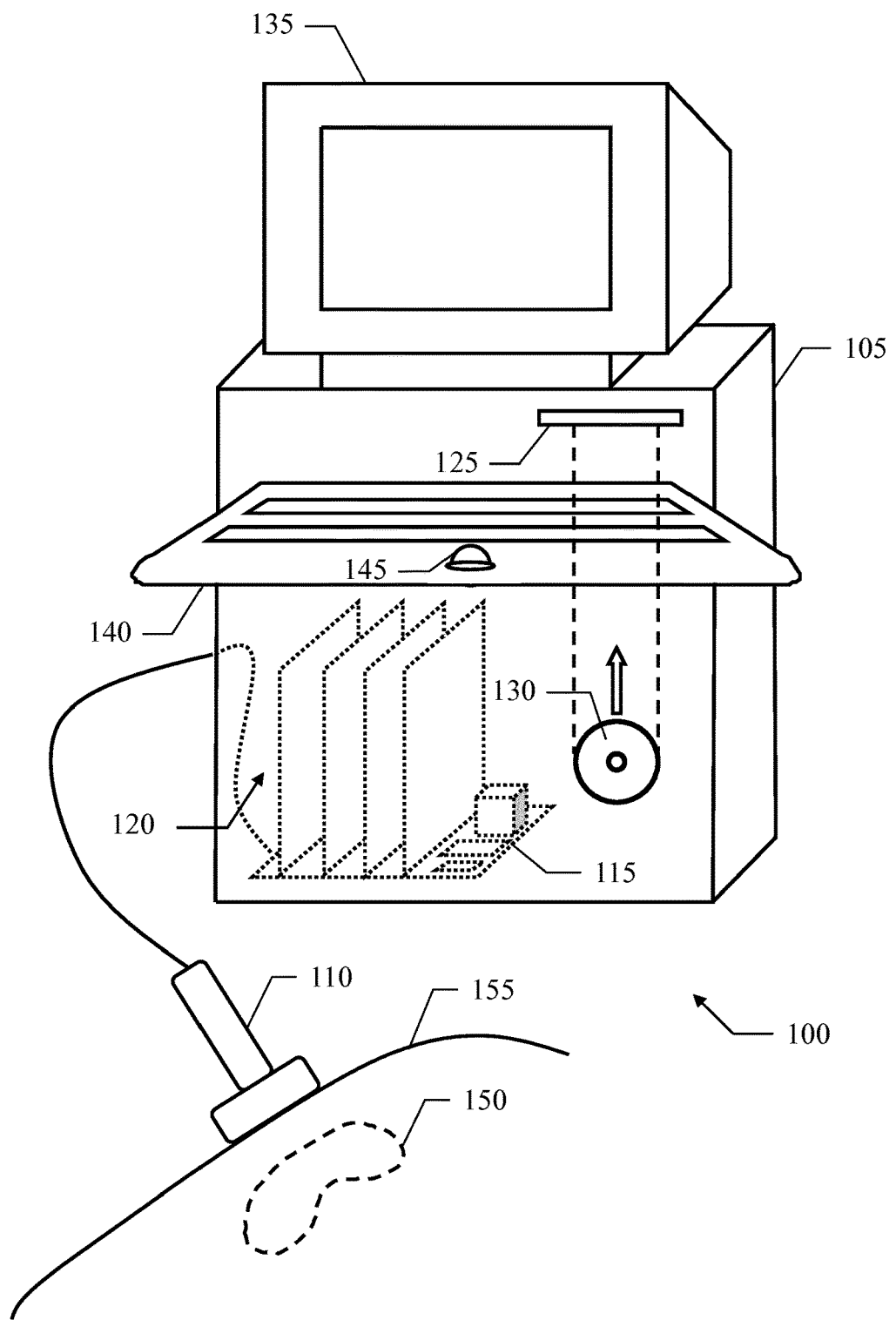
FIG. 1 shows a pictorial representation of an ultrasound scanner that may be used to practice the solution according to an embodiment of the present disclosure.

With reference to FIG. 1, a pictorial representation is shown of an ultrasound scanner 100 that may be used to practice the solution according to an embodiment of the present disclosure.

The ultrasound scanner 100 comprises a central unit 105 and a hand-held transmit-receive imaging probe, or transducer, 110 of the array type connected thereto. The transducer 110 operates in a pulse-echo mode, wherein a transmit/receive multiplexer alternatively enables a transmitter, for transmitting ultrasound pulses (for example, having a center frequency of 4-20 Hz), and a receiver, for receiving (Radio Frequency, RF) echo signals resulting from a reflection of the ultrasound pulses.

The central unit 105 houses a motherboard 115, on which electronic circuits controlling operation of the ultrasound scanner 100 are mounted (for example, a microprocessor, a working memory and a drive for a mass memory, such as a hard disk). Moreover, one or more daughter boards (denoted as a whole with the reference 120) are plugged in the motherboard 115; the daughter boards 120 provide further electronic circuits for driving the transducer 110 and for processing the echo signals. The central unit 105 is also equipped with a drive 125 for reading/writing removable storage units 130 (for example, optical disks). A monitor 135 displays images relating to an analysis process that is in progress. Operation of the ultrasound scanner 100 is controlled by means of a keyboard 140, which is connected to the central unit 105 in a conventional manner; preferably, the keyboard 140 is provided with a trackball 145 that is used to manipulate the position of a pointer (not shown in the figure) on the monitor 135.

The ultrasound scanner 100 is used to analyze a body-part 150 of a patient 155. For this purpose, an (ultrasound) contrast agent is administered to the patient 155. The contrast agent comprises particles acting as ultrasound reflectors. For example, the contrast agent is a suspension of gas-filled bubbles in a liquid carrier; typically, the gas-filled bubbles have diameters approximately of 0.1-5 μm, so as to allow their retaining within the vascular system of the patient 155, but at the same time to allow their passage through the capillaries of the patient 155. The gas-filled bubbles are generally stabilized by entraining or encapsulating the gas or a precursor thereof into a variety of systems, comprising phospholipids, emulsifiers, oils, thickeners, sugars, proteins or polymers; stabilized gas-filled bubbles are generally referred to as microvesicles. Particularly, microvesicles dispersed in an aqueous medium and bounded at the gas/liquid interface by a very thin envelope involving a surfactant (i.e., an amphiphilic material) are also known as microbubbles; alternatively, microvesicles surrounded by a solid material envelope formed by lipids or (natural or synthetic) polymers are also known as microballoons or microcapsules. Another kind of contrast agent comprises a suspension of porous microparticles of polymers or other solids, which carry bubbles of gas entrapped within the pores of the microparticles, or adsorbed on their surfaces. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467 (the entire disclosures of which are herein incorporated by reference). An example of a commercial contrast agent comprising microvesicles is SonoVue by Bracco International BV (trademarks).

The contrast agent is substantially free to circulate within the patient 155 (for example, not remaining in the same position for more than 0.1-0.5 s), but at the same time it is capable of reaching a specific (biological) target and then remaining substantially immobilized thereon (for example, staying in the same position for at least 10-30 s). For example, this result is achieved by means of a targeted contrast agent (formulated for attaching to the corresponding target), and particularly by means of a target-specific contrast agent that incorporates a target-specific ligand capable of selectively binding (for example, through biochemical affinity and/or electrostatic interaction) to a desired tissue or receptor. Examples of these target-specific ligands (which may be inserted into a membrane of the microbubbles) are monoclonal antibodies, peptides, or polysaccharides. The term tissue comprises (within its meaning) individual cells as well as aggregates of cells, such as membranes or organs. The term refers to either normal (healthy) or abnormal (pathological) cells or aggregates of cells. Examples of tissue are myocardial tissue (comprising myocardial cells and cardiomyocytes), membranous tissue (such as endothelium and epithelium), and connective tissue; examples of pathological tissue are infarcted heart tissue, blood clots, atherosclerotic plaques, inflammatory tissue and tumoral tissue. The receptors comprise any molecular structure located on the tissue (for example, within the cells or on their surfaces), which is capable of selectively binding to a specific substance. Exemplary receptors are glycoprotein GPIIbIIIa or fibrin (for example, located in blood clots or thrombi), P-Selectin (for example, located on activated endothelium of inflamed tissue) or VEGFR2 (for example, located in tumoral tissue). Examples of suitable target-specific contrast agents and of target-specific ligands are described in "G. M. Lanza and S. A. Wickline, Targeted Ultrasonic Contrast Agents for Molecular Imaging and Therapy, Progress in Cardiovascular Diseases, 44 (1), 2001, 13-31", and in WO-A-2006018433 (the entire disclosures of which are herein incorporated by reference).

During the analysis process, the (targeted) contrast agent is administered to the patient 155, for example, intravenously as a bolus (i.e., a single dose provided by an operator of the ultrasound scanner 100 with a syringe over a short period of time, of the order of 2-20 s); as a consequence, the contrast agent circulates within the vascular system of the patient 155, so as to perfuse the body-part 150. At the same time, the transducer 110 is placed in contact with a skin of the patient 155 in the area of the body-part 150, and a sequence of ultrasound pulses with low acoustic energy is applied to the body-part 150 (for example, with low mechanical index MI=0.01-0.1, so as to involve a negligible destruction of the contrast agent, for example, less than 20%, and preferably less than 10% of its total amount). The echo signal that is recorded in response to the ultrasound pulses over time provides a representation of the body-part 150 during the analysis process, for example, in the form of a sequence of images (or frames) thereof, hereinafter referred to as original images.

With reference to FIG. 2A-FIG. 2F, the general principles are shown of the solution according to an embodiment of the present disclosure.

Figure 2A:
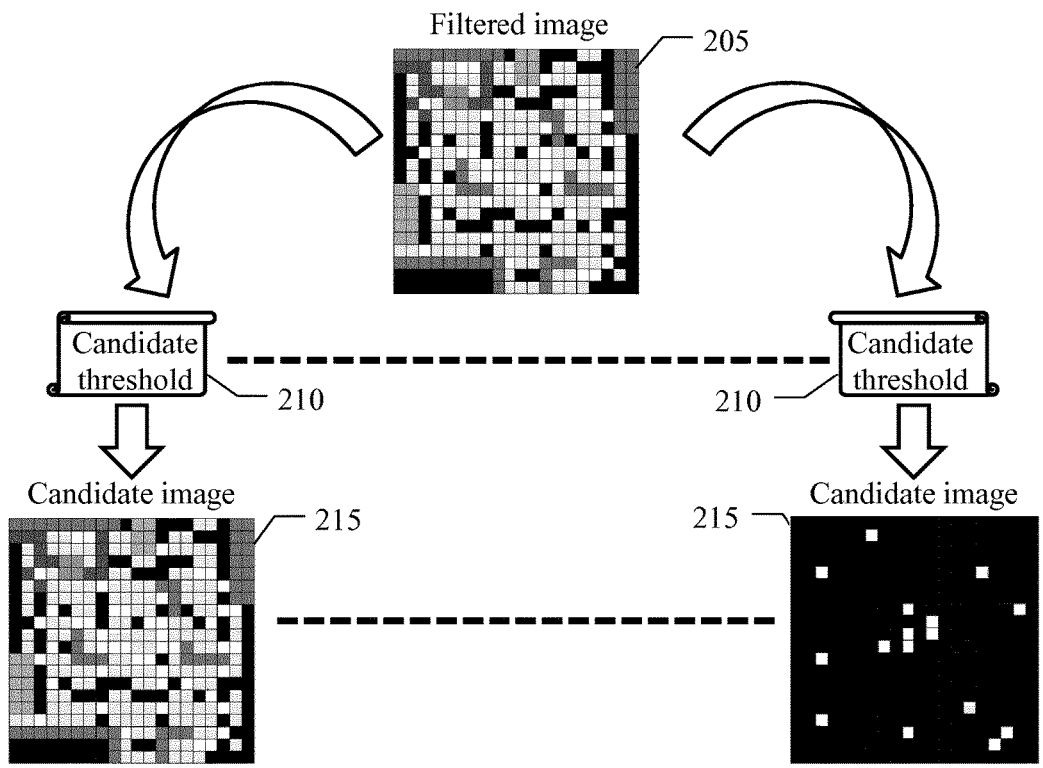
FIG. 2A-FIG. 2F show the general principles of the solution according to an embodiment of the present disclosure.

Starting from FIG. 2A, a filtered image 205 (or more) is provided. The filtered image 205 comprises a plurality of filtered values for corresponding locations of the body-part; each filtered value comprises an indication of the immobilized contrast agent at the corresponding location, with a contribution of the circulating contrast agent that has been substantially reduced (for example, when the filtered image 205 has been generated from the original images as described in WO-A-2007/054544). Moreover, a plurality of candidate values of an amplitude threshold to be used for thresholding the filtered image 205, hereinafter referred to as candidate thresholds 210, is provided (for example, by setting the candidate thresholds 210 to corresponding percentages of a base threshold calculated from the original images used to generate the filtered image 205).

At this point, a plurality of candidate images 215 corresponding to the candidate thresholds 210 is generated. Each candidate image 215 comprises a plurality of candidate values corresponding to the filtered values; the candidate image 215 is generated by setting each candidate value to the corresponding filtered value or to a reset value, for example, a lower bound value equal to zero (black in the figure), according to a comparison of the filtered value with the candidate threshold 210 (for example, by resetting to zero all the filtered values that are lower than the candidate threshold 210). As a result, in the different candidate images 215 the number of candidate values that are reset to zero changes according to the corresponding candidate thresholds 210; particularly, the number of reset candidate values is lower when the candidate threshold 210 is low (down to none when it is equal to zero) whereas it is higher when the candidate threshold 210 is high (for example, increasing as shown in the figure moving from the left to the right).

Figure 2B:
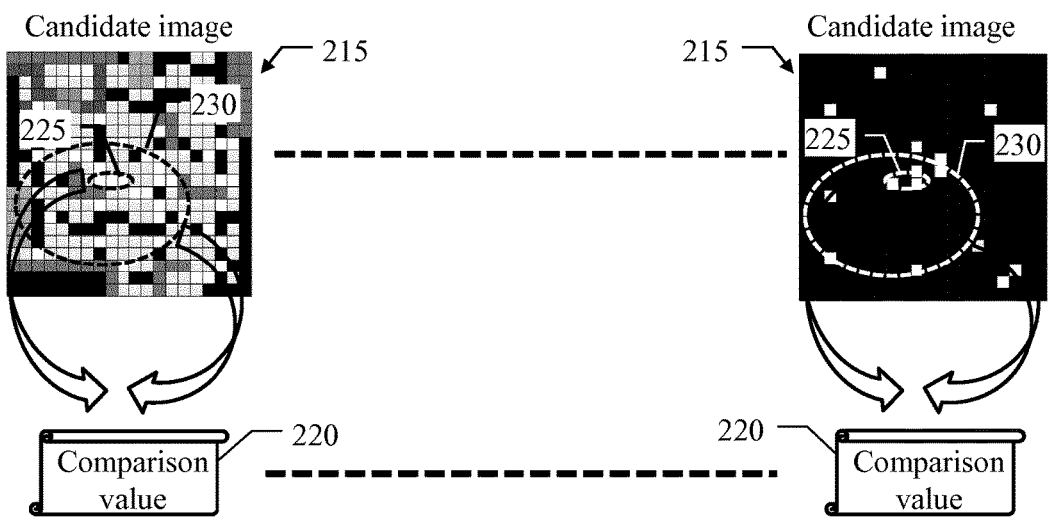

Passing to FIG. 2B, a plurality of comparison values 220 corresponding to the candidate images 215 is calculated. Each comparison value 220 is calculated according to a (further) comparison between the candidate values in an immobilization region 225 and in a circulation region 230; the immobilization region 225 corresponds to a group of locations containing a significant amount of the immobilized contrast agent (for example, selected manually) and the circulation region 230 corresponds to the locations (for example, in a Region of Interest (ROI) for the analysis process) excluding the immobilization region 225.

Figure 2C:
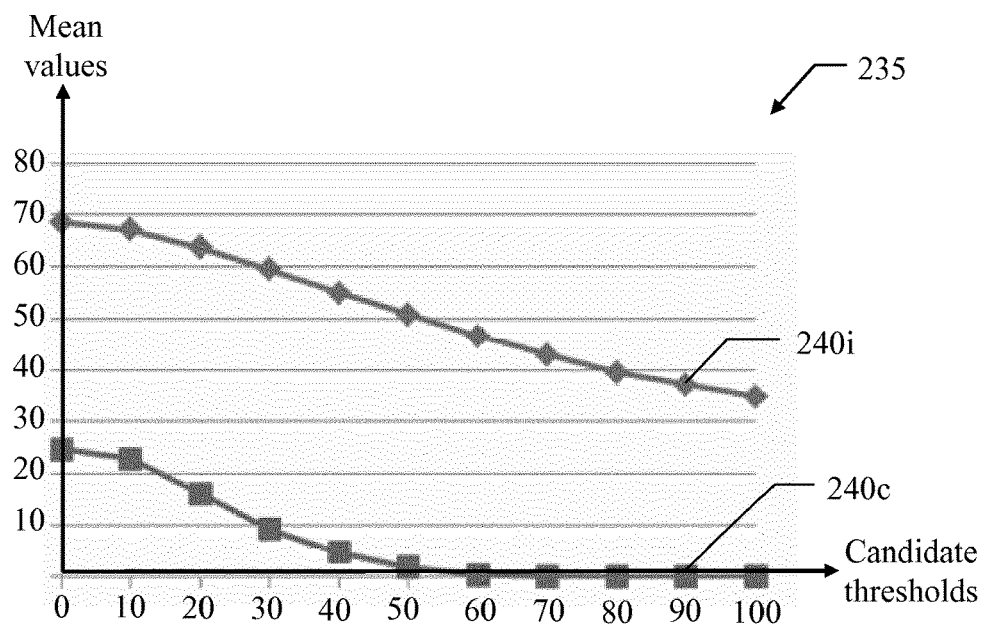

In a specific implementation, for each candidate image 215 the candidate values in the immobilization region 225 are consolidated, for example, into their mean value (hereinafter, referred to as immobilization mean value); in this way, the immobilization mean value provides a measurement of a contribution of the immobilized contrast agent that remains in the candidate image 215 after its thresholding with the corresponding candidate threshold. Likewise, the candidate values in the circulation region 230 are consolidated, for example, into their mean value as well (hereinafter, referred to as circulation mean value); in this way, the circulation mean value provides a measurement of any other contribution, mainly due to a residual contribution of the circulating contrast agent, that remains in the candidate image 215 after its thresholding with the corresponding candidate threshold. With reference to FIG. 2C, a common diagram 235 is shown that plots the immobilization mean values 240*i* and the circulation mean values 240*c* on the ordinate axis against the candidate thresholds on the abscissa axis (all of them in arbitrary units). Generally, the immobilization mean values 240*i* are higher than the circulation mean values 240*c*. Moreover, the circulation mean values 240*c* decrease quite fast (as the candidate thresholds increase) until they reach a minimum thereof, after that the circulation mean values 240*c* remain constant; the immobilization mean values 240*i* instead decrease more slowly (than the circulation mean values 240*c* do before reaching their minimum). This is due to the fact that the contribution of the immobilized contrast agent measured by the immobilization mean values 240*i* is higher than the residual contribution of the circulating contrast agent measured by the circulation mean values 240*c* (because the contribution of the circulating contrast agent has been substantially reduced in the filtered image).

Figure 2D:
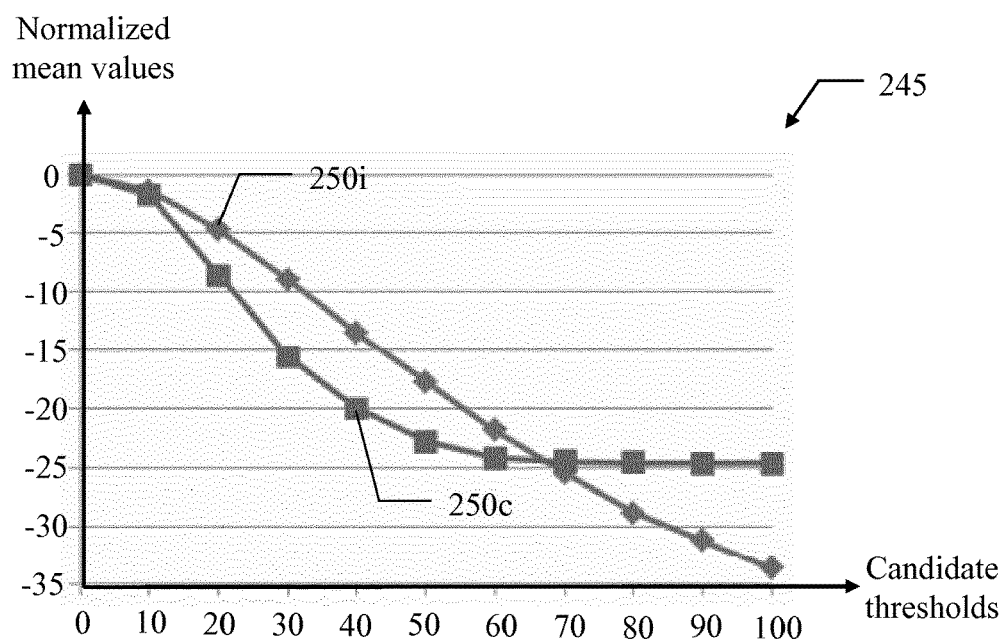

The immobilization mean values 240*i* and the circulation mean values 240*c* may also be normalized to an immobilization offset and to a circulation offset, respectively, for example, by subtracting their values in a candidate image corresponding to the candidate threshold of zero (i.e., equal to the filtered image without any thresholding). For each candidate image, the comparison value is then calculated as the difference between the normalized immobilization mean value and the normalized circulation mean value; in this way, the comparison value provides a measurement of the capacity of the corresponding candidate threshold to discriminate the contribution of the immobilized contrast from the residual contribution of the circulating contrast agent. With reference to FIG. 2D, another common diagram 245 is shown that plots the normalized immobilization mean values 250$i$ and the normalized circulation mean values 250$c$ on the ordinate axis against the candidate thresholds on the abscissa axis (all of them in arbitrary units). As above, the normalized circulation mean values 250$c$ decrease quite fast (as the candidate thresholds increase) until they reach a minimum thereof (after that the normalized circulation mean values 250$c$ remain constant); the normalized immobilization mean values 250$i$ instead decrease more slowly (than the normalized circulation mean values 250$c$ do before reaching their minimum). In this case, both the normalized immobilization mean values 250$i$ and the normalized circulation mean values 250$c$ start from zero (because of their normalization), and the normalized immobilization mean values 250$i$ fall below the normalized circulation mean values 250$c$ after the latter ones reach the corresponding minimum (because the normalized immobilization mean values 250$i$ instead continue decreasing).

Figure 2E:
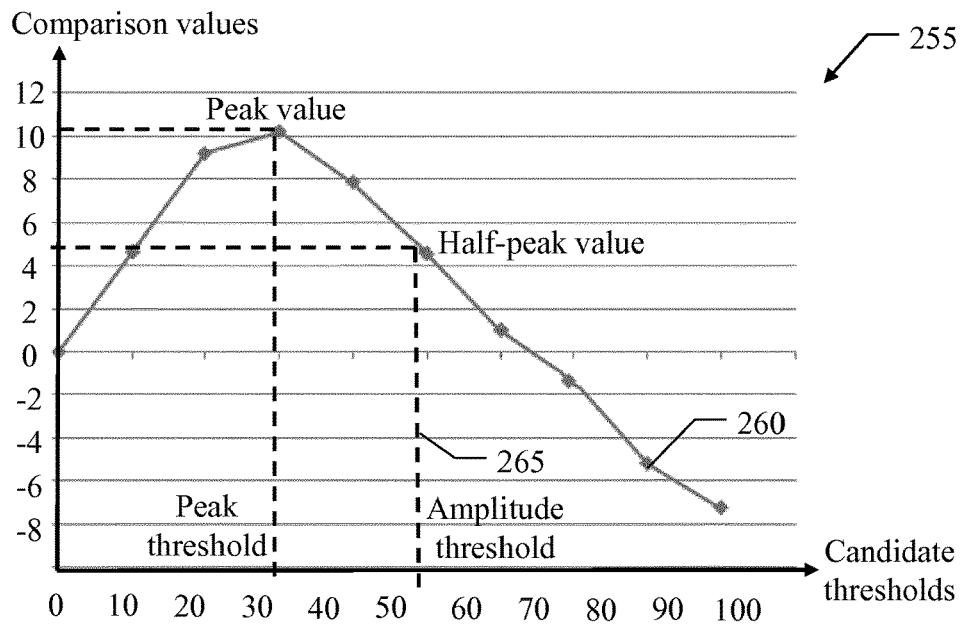

At this point, a peak of the comparison values is determined. With reference to FIG. 2E, a diagram 255 is shown that plots the comparison values 260 on the ordinate axis against the candidate thresholds on the abscissa axis (both of them in arbitrary units). In view of the above, the comparison values 260 increase (starting from zero) and then decrease (becoming negative as well) as the candidate threshold increases; particularly, the comparison values 260 reach their peak value (i.e., their absolute maximum) at one of the candidate thresholds, hereinafter referred to as peak threshold. An amplitude threshold 265 (to be used for thresholding the filtered image) is then selected at a value that is high enough to remove most of the residual contribution of the circulating contrast agent but that it is not too high to substantially affect the contribution of the immobilized contrast agent; for example, the amplitude threshold 265 is set to a value that is higher than the peak threshold and that provides a half-peak value (i.e., maximum/2) of the comparison values 260.

Figure 2F:
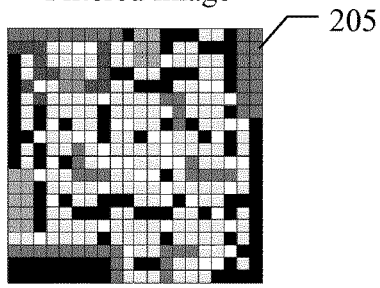
Figure 2F:
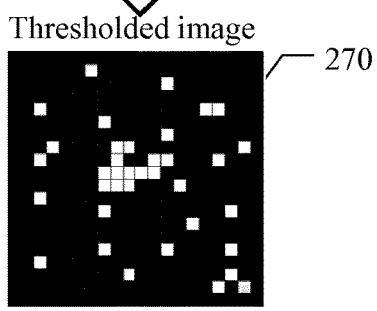

Passing to FIG. 2F, a thresholded image 270 is generated. The thresholded image 270 comprises a plurality of thresholded values corresponding to the filtered values of the filtered image 205; the thresholded image 270 is generated as above by setting each thresholded value to the corresponding filtered value or to zero (black in the figure) according to the same comparison of the filtered value with the amplitude threshold 265 (i.e., by resetting to zero all the filtered values that are lower than the amplitude threshold 265).

As a result, the amplitude threshold 265 self-adapts dynamically to the specific filtered image 205, and then to corresponding imaging conditions (for example, gain and dynamics of the ultrasound scanner, concentration of the targeted contrast agent). This significantly increases a robustness of the analysis process, since it avoids (or at least substantially reduces) the risk of having the amplitude threshold 265 too low, and then ineffective in reducing the residual contribution of the circulating contrast agent, or too high, and then reducing the contribution of the immobilized contrast agent as well.

All of the above fosters the clinical application of medical imaging techniques based on the use of targeted contrast agents.

Figure 3A:
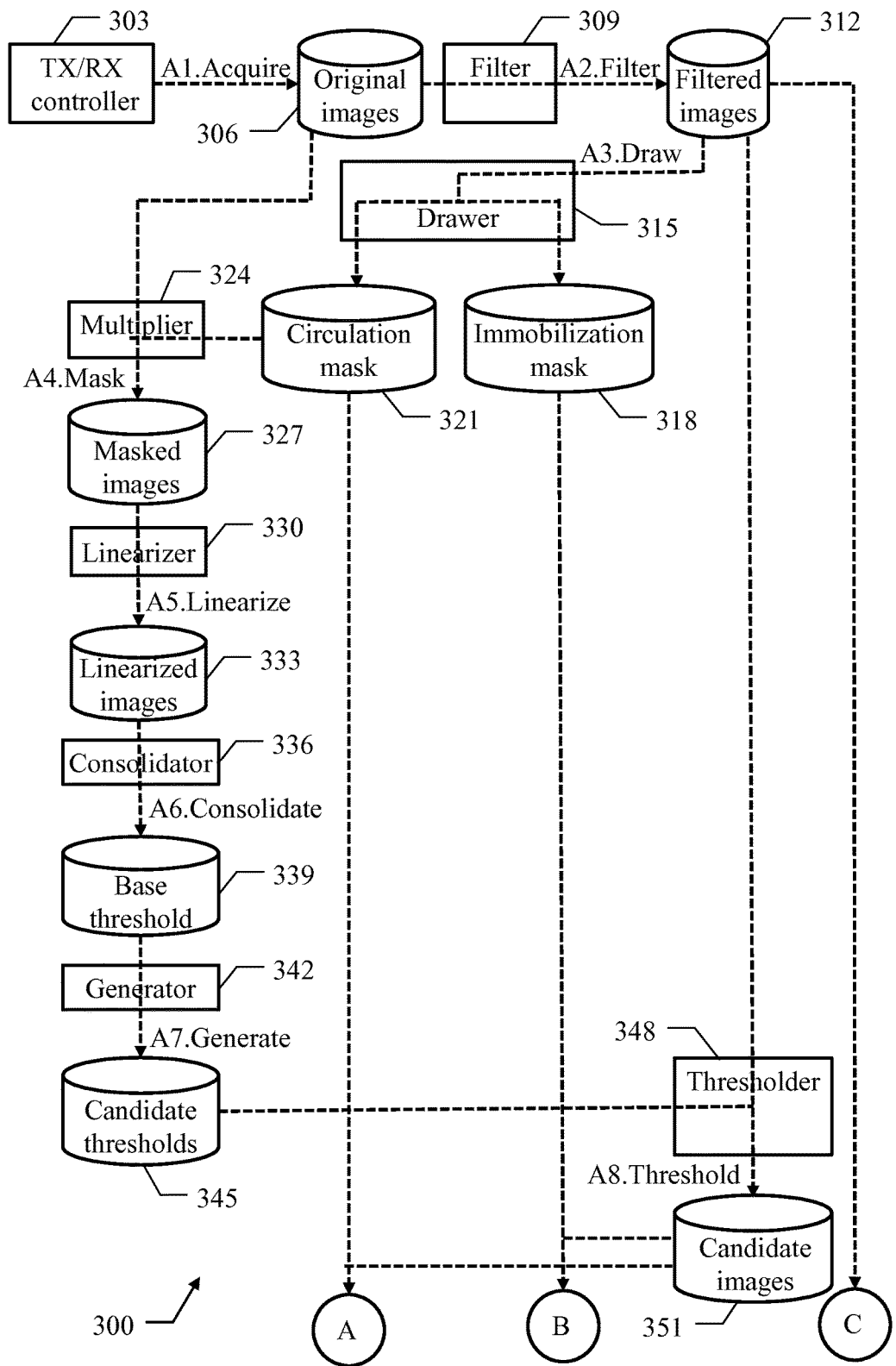
FIG. 3A-FIG. 3B show a collaboration diagram representing the roles of the main software components that may be used to implement the solution according to an embodiment of the present disclosure.
Figure 3B:
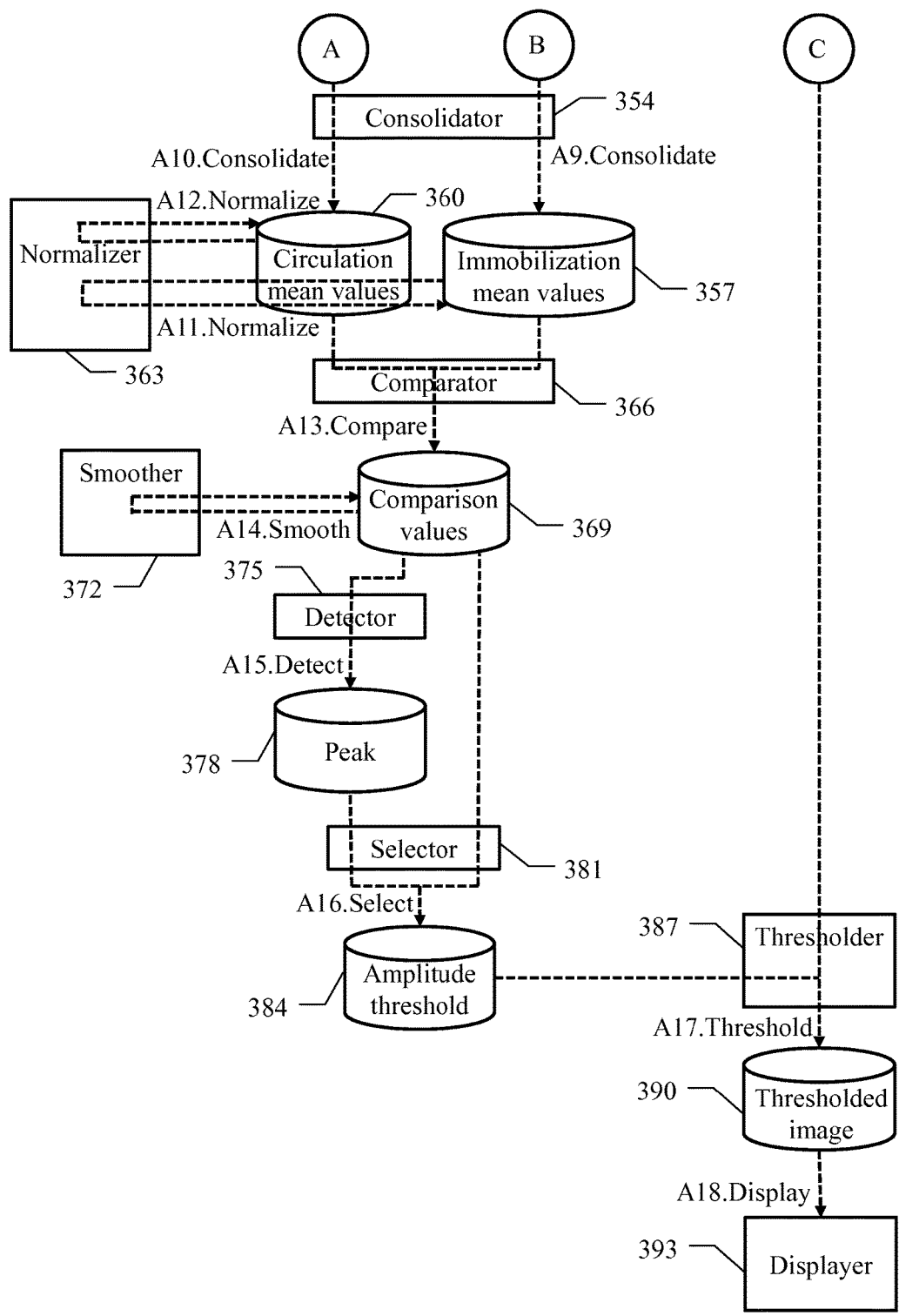

With reference to FIG. 3, a collaboration diagram is shown representing the roles of the main software components that may be used to implement the solution according to an embodiment of the present disclosure.

All the software components (programs and data) are denoted as a whole with the reference 300. The software components are typically stored in the mass memory and loaded (at least partially) into the working memory of the ultrasound scanner when the programs are running, together with an operating system and other application programs (not shown in the figure). The programs are initially installed into the mass memory, for example, from removable storage units or from a network. In this respect, each software component may represent a module, segment or portion of code, which comprises one or more executable instructions for implementing the specified logical function. Particularly, the figure describes both the static structure of the software components and their dynamic behavior (by means of a series of exchanged messages, each one representing a corresponding action, denoted with sequence numbers preceded by the symbol "A").

A TX/RX controller 303 controls the transducer of the ultrasound scanner. For example, the TX/RX controller 303 comprises a TX controller with a transmit beam former and pulsers for generating ultrasound pulses (with low MI) at successive acquisition instants (for example, with a rate of 10-30 per second). The TX/RX controller 303 further comprises an RX processor for receiving corresponding (analog RF) echo signals at each acquisition instant (for corresponding locations in a selected scan plane). The RX processor pre-amplifies the echo signals and applies a preliminary time-gain compensation (TGC); the RX processor then converts the echo signals into digital values by an Analog-to-Digital Converter (ADC), and combines them into focused beam signals through a receive beam former. The RX processor preferably processes the (digital RF) echo signals so obtained through further digital algorithms and other linear or non-linear signal conditioners (for example, a post-beam-forming TGC). Particularly, the TX/RX controller 303 operates in a contrast-specific imaging mode so as to substantially remove, or at least reduce, the dominant (linear) contribution of the tissues in the echo signals, with respect to the (non-linear) contribution of the (circulating and immobilized) contrast agent; examples of contrast-specific imaging modes comprise harmonic imaging (HI), pulse inversion (PI), power modulation (PM) and contrast pulse sequencing (CPS) techniques, for example, as described in "Rafter et al., Imaging technologies and techniques, Cardiology Clinics 22 (2004), pp. 181-197" (the entire disclosure of which is herewith incorporated by reference). The TX/RX controller 303 further comprises a video converter that demodulates, log-compresses and scan-converts the echo signals into a video format, so as to generate a (digital) image in standard Brightness mode (B-mode) of a slice of the body-part defined by the scan plane at each acquisition instant. Each image is defined by a bitmap comprising a matrix of cells (for example, with 512 rows and 512 columns) each one storing the value of a respective pixel, i.e., a basic picture element corresponding to a location consisting of a basic portion of the body-part. Each pixel value defines the brightness of the pixel as a function of an intensity of the echo signal that has been recorded for the location at the acquisition instant; for example, in images of gray scale type the pixel value may be coded on 8 bits, increasing from 0 (black) to 255 (white) as the intensity of the echo signal increases.

At the beginning of any analysis process (not shown in the figure for the sake of simplicity), the operator of the ultrasound scanner actuates the transducer and then s/he moves it around the body-part to be analyzed (before administering any contrast agent). The corresponding images that are acquired then provide an anatomical representation of the body-part, hereinafter referred to as anatomical images; these anatomical images are displayed in succession on the monitor of the ultrasound scanner in real-time. The operator then selects (in one arbitrarily chosen anatomical image) a scan plane representing a slice of the body-part to be analyzed, and possibly a region of interest thereof (for example, comprising a suspected lesion). At this point, the operator administers the contrast agent to the patient (while maintaining the transducer in a fixed position corresponding to the selected scan plane) and enters a command for starting the analysis of the body-part. In response thereto, the TX/RX controller 303 saves the corresponding images that are acquired, now defining the original images, in succession into an original image repository 306 (action "A1.Acquire").

A filter 309 generates the filtered images from the original images (extracted from the original image repository 306) as described in WO-A-2007/054544. Briefly, the filter 309 masks the original images by resetting their original values outside the region of interest to zero, sub-samples the (masked) original images and generates a corresponding (sub-sampled) filtered image for each (sub-sampled masked) original image by applying the modified Min_IP algorithm; for this purpose, the filter 309 sets each filtered value of the filtered image to the minimum among the corresponding original values in a filtering set of original images consisting of the corresponding original image and one or more preceding original images (for example, 1-5 preceding original images corresponding to a filtering window of 0.1-0.5 s). The filter 309 overlays the filtered images on the corresponding original images and then restores their full size. The filter 309 saves the (overlaid) filtered images in succession into a filtered image repository 312. At the same time (not shown in the figure for the sake of simplicity), the filtered images are displayed in succession on the monitor of the ultrasound scanner substantially in real-time, with a short delay corresponding to the filtering window (action "A2.Filter"). Alternatively (not shown in the figure), the filtered images may be simply received from another device (for example, through a removable storage unit or a digital, analogue or network connection) or from another software program (running on the same or a different device) and then stored in the filtered image repository 312 directly. In any case, the filtered images may be obtained by applying any other filtering technique (for example, the differential targeted enhancement one) or even simply waiting until most of the circulating contrast agent has disappeared (i.e., with the filtered images that are defined directly by the original images at a delayed phase). In other words, the filtered images are the starting point (irrespectively of whether they are actually generated, either locally or remotely, or they are provided already in this form).

A drawer 315 is used by the operator to draw (in one arbitrarily chosen filtered image extracted from the filtered image repository 312) the circulation region and the immobilization region. Preferably, the circulation region is drawn as larger as possible but excluding any specular reflectors (with the possibility of simply considering it equal to the region of interest); the immobilization region is then drawn inside the circulation region. The immobilization region and the circulation region are represented by an immobilization mask and by a circulation mask, respectively, each one defined by a matrix of cells with the same size as the filtered images. Each cell of the immobilization mask stores a flag (i.e., a binary value) that is asserted (for example, at the logic value 1) when the corresponding location is inside the immobilization region or it is deasserted (for example, at the logic value 0) otherwise; each cell of the circulation mask stores a flag that is asserted when the corresponding location is inside the circulation region but outside the immobilization region or it is deasserted otherwise (i.e., when the corresponding location is outside the circulation region or inside the immobilization region). The drawer 315 saves the immobilization mask and the circulation mask into an immobilization mask repository 318 and a circulation mask repository 321, respectively (action "A3.Draw").

A multiplier 324 multiplies each original image used to generate a last filtered image, i.e., the last original images defining the corresponding filtering window (extracted from the original image repository 306), and the circulation mask (extracted from the circulation mask repository 321) cell-by-cell, so as to generate a corresponding masked image. As a result, the masked image is defined by a matrix of cells with the same size as the original image; the masked image only comprises the original values that are inside the circulation region, whereas the other original values are reset to zero. The multiplier 324 saves the masked images so obtained into a masked image repository 327 (action "A4.Mask"). A linearizer 330 generates a linearized image from each masked image (extracted from the masked image repository 327). The linearized image is defined by a matrix of cells with the same size as the masked image; each cell of the linearized image inside the circulation region (i.e., whose flag in the circulation mask is asserted) stores a value that is calculated by making the corresponding (original) value in the masked image directly proportional to a local concentration of the contrast agent (for example, by applying an inverse log-compression and then squaring the value so obtained as described in WO-A-2004/110279, the entire disclosure of which is herein incorporated by reference), whereas the other cells remain at zero. The linearizer 330 saves the linearized images so obtained for the different original images into a linearized image repository 333 (action "A5.linearize"). The operations of masking the original images and/or linearizing the masked images may be omitted when the masked images and/or the linearized images are already provided by the filter 309 (for generating the filtered images).

A consolidator 336 calculates the median of the (linearized original) values of the cells inside the circulation region of each linearized image (extracted from the linearized image repository 333); the consolidator 336 then sets the base threshold (to be used for calculating the candidate thresholds) equal to the mean of the median values so obtained for the different linearized images. The consolidator 336 stores the base threshold into a base threshold variable 339 (action "A6.Consolidate"). A generator 342 calculates a predefined number of candidate thresholds (for example, 100-300, preferably 150-250 and still more preferably 175-225, such as 200), as defined by corresponding candidate values of the amplitude threshold. Particularly, the candidate thresholds are calculated by multiplying the base threshold (extracted from the base threshold variable 339) by corresponding percentages (for example, from 0-50% to 150-250%, preferably from 0-20% to 170-230% and still more preferably from 0-10% to 190-210%, such as from 0% to 199%); for example, 200 candidate thresholds are calculated by multiplying the base threshold by percentages ranging from 0% to 199% with a pitch of 1%. The generator 342 saves the candidate thresholds so obtained into a candidate threshold vector 345 (action "A7.Generate"). All of the above increases the robustness and the accuracy of the method. Particularly, the median used to calculate the base threshold provides a measure of a central tendency of the corresponding values that is not unduly affected by their outliers; as a result, the effects of any inaccuracy in the selection of the circulation region (which may introduce high values due to bright specular reflectors) are significantly mitigated. Moreover, the use of the base threshold to generate the candidate thresholds makes them depending on the original images that are used to generate the filtered images; as a result, the candidate thresholds as well self-adapt dynamically to the imaging conditions. Alternatively (not shown in the figure), the candidate thresholds are calculated in the same way from a pre-defined base threshold, even independently of the original images; for example, the base threshold is a (customizable) fixed value, or it is selected among multiple (customizable) fixed values, either manually or automatically, such as according to imaging conditions (like average quality of the original images). As a further alternative, the candidate thresholds are pre-defined directly; for example, the candidate thresholds are (customizable) fixed values, or they are selected among multiple sets of (customizable) fixed values as above.

A thresholder 348 generates the candidate image for each candidate threshold (extracted from the candidate threshold vector 345). For this purpose, the thresholder 348 generates a thresholding mask corresponding to the candidate threshold from the last filtered image (extracted from the filtered image repository 312). The thresholding mask is defined by a matrix of cells with the same size as the (last) filtered image; each cell of the thresholding mask stores a flag that is asserted when the corresponding filtered value is (possibly strictly) higher than the candidate threshold or it is deasserted otherwise. The thresholder 348 then multiplies the filtered image and the thresholding mask cell-by-cell, so as to generate the candidate image. As a result, the candidate image is defined by a matrix of cells with the same size as the filtered image; the candidate image only comprises the filtered values that are higher than the candidate threshold, whereas the other filtered values are reset to zero. The thresholder 348 saves the candidate images so obtained for the different candidate thresholds into a candidate image repository 351 (action "A8.Threshold").

A (further) consolidator 354 calculates the immobilization mean value of each candidate image (extracted from the candidate image repository 351) as the mean of the (filtered) values of its cells inside the immobilization region (i.e., whose flag is asserted in the immobilization mask extracted from the immobilization mask repository 318). The consolidator 354 stores the immobilization mean values so obtained for the different candidate thresholds into an immobilization mean value vector 357 (action "A9.Consolidate"). Likewise, the consolidator 354 calculates the circulation mean value of each candidate image (again extracted from the candidate image repository 351) as the mean of the (filtered) values of its cells inside the circulation region (i.e., whose flag is asserted in the circulation mask extracted from the circulation mask repository 321). The consolidator 354 stores the circulation mean values so obtained for the different candidate thresholds into a circulation mean value vector 360 (action "A10.Consolidate").

A normalizer 363 normalizes the immobilization mean values in the immobilization mean value vector 357; for this purpose, the normalizer 363 subtracts the immobilization offset (defined by the immobilization mean value corresponding to the candidate threshold of zero, i.e., the first one) from each immobilization mean value and then replaces the immobilization mean value with the result of this operation (action "A11.Normalize"). Likewise, the normalizer 363 normalizes the circulation mean values in the circulation mean value vector 360; for this purpose, the normalizer 363 subtracts the circulation offset (defined by the circulation mean value corresponding to the candidate threshold of zero, i.e., the first one) from each circulation mean value and then replaces the circulation mean value with the result of this operation (action "A12.Normalize").

A comparator 366 subtracts each (normalized) circulation mean value (extracted from the circulation mean value vector 360) from the corresponding (normalized) immobilization mean value (extracted from the immobilization mean value vector 357) so as to obtain the comparison value for the corresponding candidate threshold. The comparator 366 stores the comparison values so obtained for the different candidate thresholds into a comparison value vector 369 (action "A13.Compare"). A smoother 372 smooths the comparison values in the comparison value vector 369; for this purpose, the smoother 372 applies a smoothing algorithm to the comparison values for reducing their variations (for example, a moving average filter or a low pass filter) and then replaces the comparison values with the result of this operation (action "A14.Smooth").

A detector 375 scans the (smoothed) comparison values (in the comparison value vector 369) to determine their maximum (defining the peak value); the detector 375 stores the peak value and an indication of the candidate threshold providing it (defining the peak threshold), for example, the peak threshold itself or an index indicating its position in the comparison value vector 369, into a peak variable 378 (action "A15.Detect"). A selector 381 calculates the half-peak value of the comparison values by dividing the peak value (extracted from the peak variable 378) by two. The selector 381 scans the comparison values (in the comparison value vector 369) in increasing order of the candidate thresholds starting from the peak threshold, until a comparison value equal to or lower than the half-peak value is found (always occurring in practice before reaching an end of the comparison value vector 369). If the found comparison value is equal to the half-peak value, the selector 381 directly sets the amplitude threshold to the candidate threshold providing it; otherwise, the selector 381 sets the amplitude threshold to the candidate threshold that provides the comparison value closer to the half-peak value between the candidate threshold providing the found comparison value and a preceding (lower) candidate threshold. The selector 381 stores the amplitude threshold so determined into an amplitude threshold variable 384 (action "A16.Select"). This choice of the amplitude threshold has been found to provide a good compromise (between the opposed requirements of removing the residual contribution of the circulating contrast agent and not affecting the contribution of the immobilized contrast agent) in most practical situations.

At this point, a thresholder 387 (possibly the same as above) applies the amplitude threshold (extracted from the amplitude threshold variable 384) to the same (last) filtered image (extracted from the filtered image repository 312). For this purpose, the thresholder 387 generates a (further) thresholding mask corresponding to the amplitude threshold. The thresholding mask is defined by a matrix of cells with the same size as the filtered image; each cell of the thresholding mask inside the region of interest (i.e., whose flag in a corresponding mask is asserted) stores a flag that is asserted when the corresponding filtered value is (possibly strictly) higher than the amplitude threshold or it is deasserted otherwise, whereas each cell of the thresholding mask outside the region of interest stores the flag that is always asserted. The thresholder 387 then multiplies the filtered image and the thresholding mask cell-by-cell, so as to generate the corresponding thresholded image. As a result, the thresholded image is defined by a matrix of cells with the same size as the filtered image; inside the region of interest the thresholded image only comprises the filtered values that are higher than the amplitude threshold, whereas the other filtered values are reset to zero, and outside the region of interest the thresholded image comprises the filtered values (i.e., the corresponding original values). The thresholder 387 saves the thresholded image so obtained into a thresholded image repository 390 (action "A17.Threshold"). A displayer 393 displays the thresholded image (extracted from the thresholded image repository 390) on the monitor of the ultrasound scanner (action "A18.Display"). In this way, in the region of interest the thresholded image only shows the filtered values that are significant (for the detection of the immobilized contrast agent); these filtered values may also be rendered according to a given color-map palette (for facilitating the quantification of the immobilized contrast agent). Outside the region of interest, instead, the thresholded image always shows the anatomical representation of the body-part (for contextualizing the information relating to the immobilized contrast agent).

Figure 4:
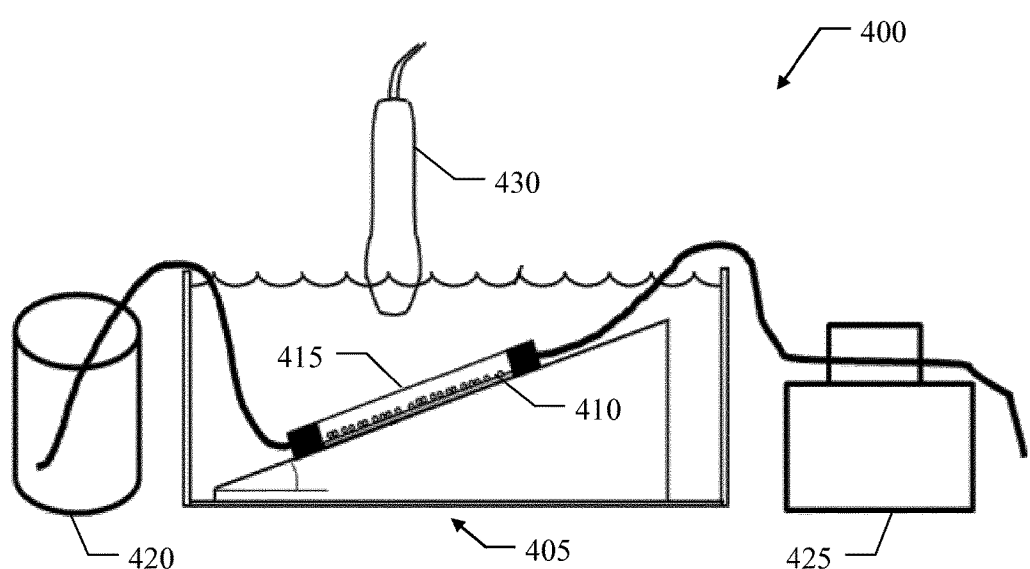
FIG. 4 shows a set-up that was used to test the solution according to an embodiment of the present disclosure in-vitro.

With reference to FIG. 4, a set-up 400 is shown that was used to test the solution according to an embodiment of the present disclosure in-vitro.

The set-up 400 comprises a (sliding) flow-cell 405; the flow-cell 405 is formed by a chamber having a bottom wall made of a glass plate 410 coated with human P-selectin Fc and an upper wall made of an acoustically transparent Mylar film 415; before mounting the flow-cell 405 in the setup 400, a (targeted) contrast agent comprising Selectin-targeted microbubbles (MB) was incubated on the glass plate 410 so as to remain immobilized thereon. A (non-targeted) contrast agent comprising BR38 microbubbles ($1 \cdot 10^5$ bubbles/mL) was circulated from a reservoir 420 through the flow-cell 405, by using a peristaltic pump 425. In this way, in-vivo conditions are mimicked wherein immobilized contrast agent is surrounded by circulating contrast agent. Original images of the flow-cell 405 (containing both the immobilized contrast agent and the circulating contrast agent) were acquired at 5 different locations using an ultrasound scanner 430 consisting of the Sequoia 512 fitted with the linear transducer 15L8 in CPS contrast-specific mode; imaging settings of the ultrasound scanner 430 were: MI 0.08, depth 25 mm, focus 15 and 17 mm, frame rate 4 Hz. Data provided by the ultrasound scanner 430 were exported as DICOM sequences; logarithmically compressed video data were linearized at the pixel level providing echo-power signals proportional to the local concentration of the contrast agent, using the calibration file 15L8, 83 dB, PP4, Delta 2, +1/M:2 (v1.1). Analyzed results were stored as XLS files. The same operations were repeated with 4 different versions of the glass plate 410, each one with two different concentrations of the (targeted) contrast agent incubated thereon, resulting in 8 different surface densities of the immobilized contrast agent ($3.3$-$97.5 \cdot 10^6$ $\mu m^2$/mL); the surface densities of the immobilized contrast agent were determined by optically counting its microbubbles (average of 5 locations).

With reference to FIG. 5A-FIG. 5F, different examples are shown of in-vitro application of the solution according to an embodiment of the present disclosure.

Figure 5A:
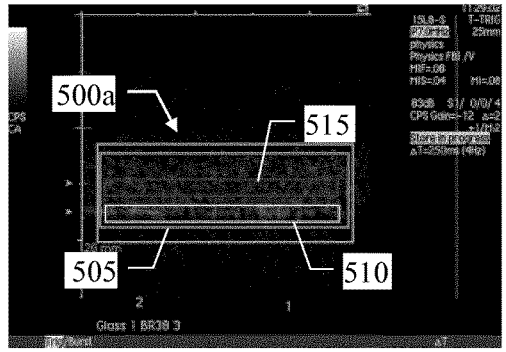
FIG. 5A-FIG. 5F show different examples of in-vitro application of the solution according to an embodiment of the present disclosure.
Figure 5B:
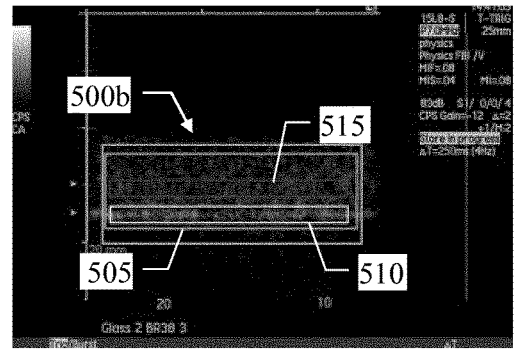

Starting from FIG. 5A and FIG. 5B, two original images 500a and 500b are shown that were acquired in the above-described set-up by imaging the flow-cell with different surface densities of the immobilized contrast agent (factor 10), i.e., low in FIG. 5A and high in FIG. 5B. In both cases, a same circulation region 505 was drawn to enclose most of the flow-cell (containing both immobilized contrast agent and circulating contrast agent), a same immobilization region 510 was drawn at a lower part of the flow-cell (primarily containing immobilized contrast agent with some circulating contrast agent) and a control region 515 was drawn inside a lumen of the flow-cell (exclusively containing circulating contrast agent). The concentration of the circulating contrast agent in the original images 500a and 500b is substantially the same (irrespectively of the different surface densities of the immobilized contrast agent).

Figure 5C:
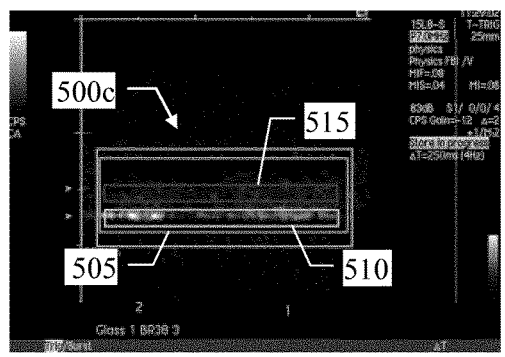
Figure 5D:
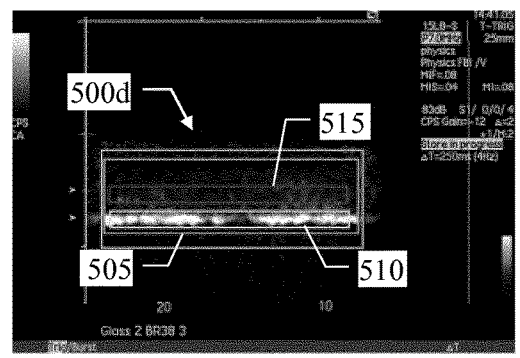

Passing to FIG. 5C and FIG. 5D, corresponding filtered images 500c and 500d are shown that were obtained by filtering these original images (corresponding to the low and the high, respectively, surface densities of the immobilized contrast agent) to reduce the contribution of the circulating contrast agent. In both cases, the immobilized contrast agent is correctly detected (as visible in the immobilization region 510). However, as expected the circulating contrast agent is not completely removed (as visible in the control region 515); this reflects in a relatively low value of an immobilized/circulating ratio (calculated by dividing the mean of the filtered values in the immobilization region 510 by the mean of the filtered values in the control region 515) equal to 3 dB and 13 dB for the low and the high, respectively, surface densities of the immobilized contrast agent.

Figure 5E:
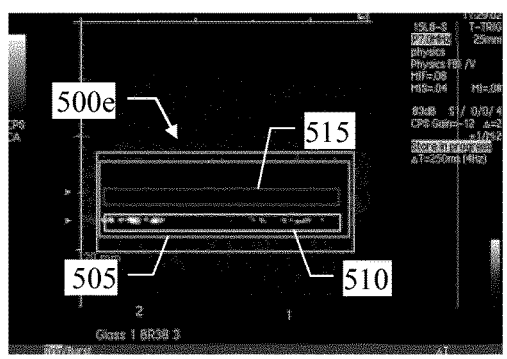
Figure 5F:
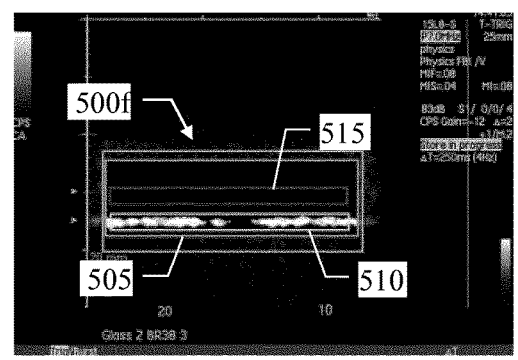

Passing to FIG. 5E and FIG. 5F, corresponding thresholded images 500e and 500f are shown that were obtained by thresholding these filtered images (corresponding to the low and the high, respectively, surface densities of the immobilized contrast agent) with an amplitude threshold determined according to the solution according to an embodiment of the present disclosure. In both cases, the immobilized contrast agent is again correctly detected (as visible in the immobilization region 510). However, the circulating contrast agent is now almost completely removed (as visible in the control region 515); this reflects in a far higher value of the immobilized/circulating ratio (calculated by dividing the mean of the thresholded values in the immobilization region 510 by the mean of the thresholded values in the control region 515) that becomes equal to 16 dB and 27 dB for the low and the high, respectively, surface densities of the immobilized contrast agent. All of the above confirms that the solution according to an embodiment of the present disclosure significantly improves the conspicuity of the immobilized contrast agent (and thus the ability to detect it).

Figure 6A:
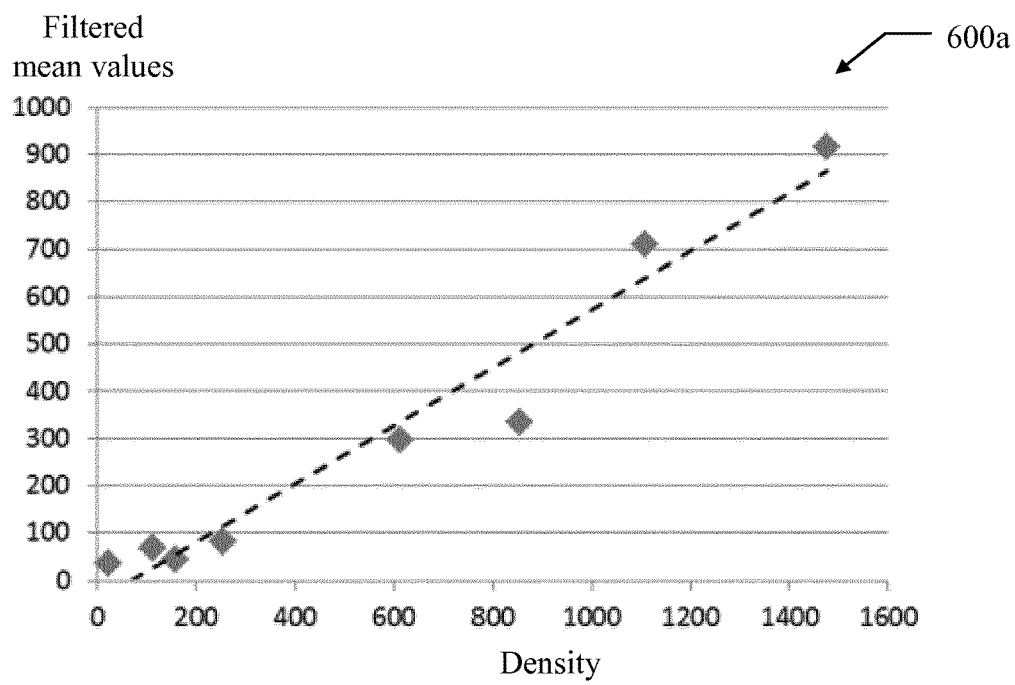
FIG. 6A-FIG. 6B show diagrams relating to different examples of in-vitro application of the solution according to an embodiment of the present disclosure.
Figure 6B:
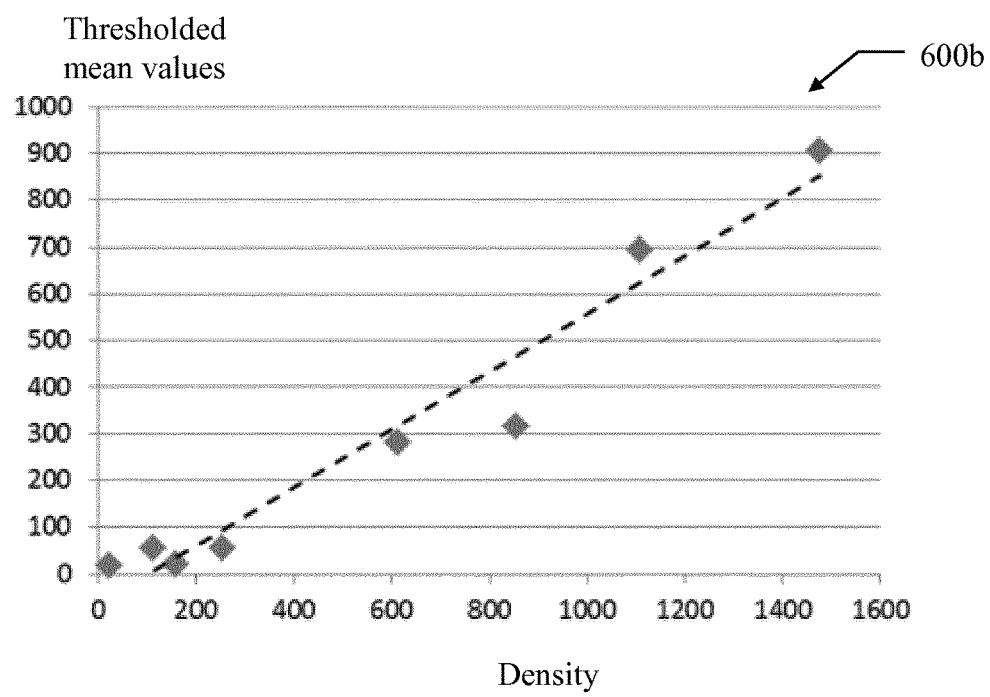

With reference to FIG. 6A-FIG. 6B, diagrams are shown relating to different examples of in-vitro application of the solution according to an embodiment of the present disclosure.

Particularly, the mean of the filtered values and the mean of the thresholded values inside the immobilization region (hereinafter referred to as filtered mean values and thresholded mean values, respectively) were calculated in the filtered images and in the thresholded images, respectively, which were obtained from the original images that where acquired in the above-described set-up by imaging the flow-cell with all the (8) different surface densities of the immobilized contrast agent. FIG. 6A shows a diagram 600a that plots the filtered mean values on the ordinate axis (in arbitrary units) against the surface densities of the immobilized contrast agent on the abscissa axis (in $mm^{-2}$) and FIG. 6B shows a diagram 600b that plots the thresholded mean values on the ordinate axis (in arbitrary units) against the surface densities of the immobilized contrast agent on the abscissa axis (in $mm^{-2}$). The obtained results are very similar, with a direct proportionality that may be observed of the filtered mean values (y) and of the thresholded mean values (y') against the surface densities of the immobilized contrast agent (x), with y=0.616x-43.542 and coefficient of determination $R^2$=0.9511 and with y'=0.6212x-64.401 and coefficient of determination $R^2$=0.9495, respectively. The similarity between the filtered mean values and the thresholded mean values (due to the fact that they have been obtained in a controlled environment with a few amount of circulating contrast agent in the immobilization region) confirms that the solution according to an embodiment of the present disclosure does not affect the amount of immobilized contrast agent that is detected and then preserves the ability to quantify it.

Figure 7A:
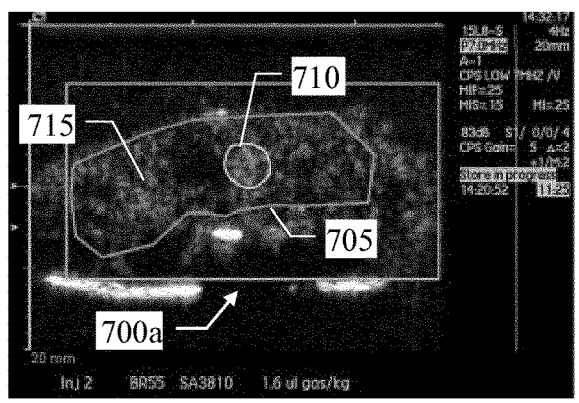
FIG. 7A-FIG. 7C show an example of in-vivo application of the solution according to an embodiment of the present disclosure.
Figure 7B:
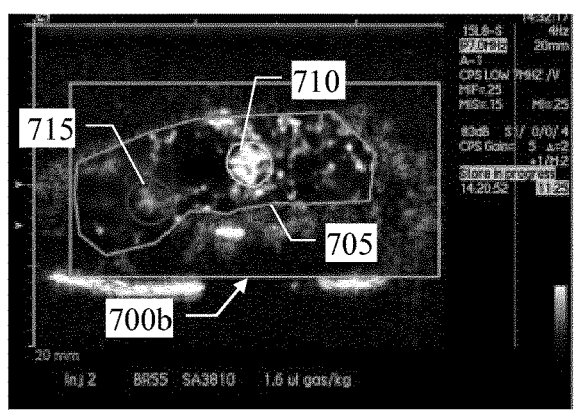
Figure 7C:
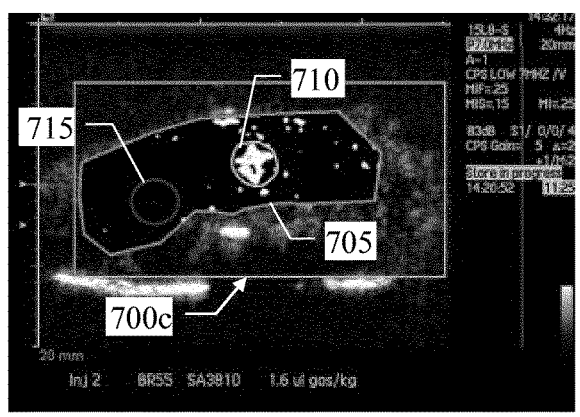

With reference to FIG. 7A-FIG. 7C, an example is shown of in-vivo application of the solution according to an embodiment of the present disclosure.

An orthotopic animal model of Human Colon carcinoma was used. A (targeted) contrast agent comprising microbubbles being target-specific for FLK1 (also known as VEGFR2) was administered intravenously at the dose of 1.6 µL/kg (expressed as gas volume). Original images of the body-part comprising the carcinoma were acquired (during late phase enhancement, more than 10 minutes after administration of the contrast agent) using an ultrasound scanner consisting of the Siemens Sequoia 512 fitted with the linear transducer 15L8 in CPS contrast-specific mode; imaging settings of the ultrasound scanner were: MI 0.25, frame rate 4 Hz. Data provided by the ultrasound scanner were exported as DICOM sequences; logarithmically compressed video data were linearized at the pixel level providing echo-power signals proportional to the local concentration of the contrast agent, using the calibration file 15L8, CPS, 83 dB, PP4, Delta 2, +1/M:2 (v1.1).

Starting from FIG. 7A, an exemplary original image 700a is shown (which was acquired by imaging the body-part more than 10 minutes after the administration of the contrast agent). A circulation region 705 was drawn to contain most of the body-part (comprising the carcinoma and surrounding tissues, but excluding specular reflectors), an immobilization region 710 was drawn inside the circulation region 705 to contain the carcinoma only and a control region 715 was drawn inside the circulation region 705 but far away from the carcinoma (such that it would contain primarily circulating contrast agent only). Despite the substantial delayed phase expecting the circulating contrast agent to be cleared, the original image 700a still comprises, besides the immobilized contrast agent in the immobilization region 710, a substantial amount of circulating contrast agent outside it. This limits the conspicuity of the immobilized contrast agent (and thus the ability to detect it), as reflected by a low value of the immobilized/circulating ratio (calculated by dividing the mean of the original values in the immobilization region 705 by the mean of the original values in the control region 715) equal to 3 dB.

Passing to FIG. 7B, a corresponding filtered image 700b is shown that was obtained by filtering this original image to reduce the contribution of the circulating contrast agent. The immobilized/circulating ratio (calculated by dividing the mean of the filtered values in the immobilization region 705 by the mean of the filtered values in the control region 715) increases to 11 dB, but the circulating contrast agent is not completely removed yet (as visible in the control region 715).

Passing to FIG. 7C, a corresponding thresholded image 700c is shown that was obtained by thresholding this filtered image with an amplitude threshold determined according to the solution according to an embodiment of the present disclosure. The immobilized/circulating ratio (calculated by dividing the mean of the thresholded values in the immobilization region 705 by the mean of the thresholded values in the control region 715) now increases to 21 dB and the circulating contrast agent is almost completely removed (as visible in the control region 715); this significantly improves the conspicuity of the immobilized contrast agent, and thus the ability to detect it in correspondence to the carcinoma.

Modifications

Naturally, in order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof; conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items), the terms based on, dependent on, according to, function of (and any forms thereof) should be intended as a non-exclusive relationship (i.e., with possible further variables involved), the term a/an should be intended as one or more items (unless expressly indicated otherwise), and the term means for (or any means-plus-function formulation) should be intended as any structure adapted or configured for carrying out the relevant function.

For example, an embodiment provides a method for analyzing a body-part of a patient; the body-part has been perfused before performing the method with a contrast agent capable of circulating within the patient and of being substantially immobilized on a biological target. However, the method may be used to analyze any body-part of any patient (see below). Moreover, the contrast agent may be of any type (for example, specific for enhancing Magnetic Resonance imaging or X-ray Computed Tomography imaging) and even not of the targeted type, when it is conveyed or accumulated to the target by means of a non-specific interaction therewith (for example, when the contrast agent is recognized as a foreign substance by the immune system of the patient and then transported to the liver for its metabolism and elimination); moreover, the contrast agent may have been administered in any way (for example, as a continuous infusion by a pump) and at any time (for example, immediately before performing the method). In any case, this is a data-processing method that may be implemented independently of any interaction with the patient; moreover, the contrast agent may also be administered to the patient in a non-invasive manner (for example, orally for imaging the gastro-intestinal tract or via a nebulizer into the airways), or in any case without any substantial physical intervention thereon that would require professional medical expertise or entail any health risk for the patient (for example, intramuscularly). Although the method may facilitate the task of a physician, it only provides intermediate results that may help him/her in examining the body-part (for example, for diagnostic purposes) but with the diagnosis for curative purposes stricto sensu that is always made by the physician himself/herself.

In an embodiment, the method comprises providing at least one filtered image comprising a plurality of filtered values for corresponding locations of the body-part; each filtered value comprises an indication of the immobilized contrast agent at the corresponding location with a contribution of the circulating contrast agent that has been substantially reduced. However, the filtered image may be provided in any way (for example, generating it locally or receiving it already in this form). Any number of filtered images may be provided (for example, by applying the method to the whole sequence of filtered images). Each filtered image may have any size and shape (from a whole matrix to one or more portions thereof), and its filtered values may correspond to any type of locations of the body-part (for example, pixels, voxels or groups thereof when the filtered image is sub-sampled). The filtered values may indicate the immobilized contrast agent at the corresponding location (if any) in any way (for example, in negative form when they decrease with the intensity of the echo signal) and the contribution of the circulating contrast agent may have been reduced at any level (for example, by at least 50-90%) in any way, even automatically when the filtered image is acquired at a delayed phase.

In an embodiment, the method comprises generating a thresholded image comprising a plurality of thresholded values corresponding to the filtered values; the thresholded image is generated by setting each thresholded value to the corresponding filtered value or to a reset value according to a comparison of the filtered value with an amplitude threshold. However, the reset value may be any lower or higher bound value of the filtered values (for example, a maximum value when the filtered images are in negative form); moreover, the comparison with the amplitude threshold may be performed in any way (for example, on a sub-sampled version of the filtered image, on the whole filtered image or only on one or more parts thereof).

In an embodiment, the method comprises providing a plurality of candidate thresholds defined by corresponding candidate values of the amplitude threshold. However, the candidate thresholds may be in any number and they may be provided in any way, even independently of the original images.

In an embodiment, the method comprises generating a plurality of candidate images corresponding to the candidate thresholds each one comprising a plurality of candidate values corresponding to the filtered values; each candidate image is generated by setting each candidate value to the corresponding filtered value or to the reset value according to said comparison of the filtered value with the candidate threshold. However, the comparison may be performed in any way (either equal or not to the one used to generate the thresholded image, for example, at the level of different parts of the filtered image).

In an embodiment, the method comprises calculating a plurality of comparison values corresponding to the candidate images; the comparison value of each candidate image is calculated according to a further comparison between the candidate values in an immobilization region corresponding to a group of locations containing a significant amount of the immobilized contrast agent and the candidate values in a circulation region corresponding to at least part of the locations excluding the immobilization region. However, the comparison values may be calculated in any way, even without consolidating the candidate values in the immobilization region and/or in the circulation region (for example, by simply summing the candidate values in the immobilization region minus the candidate values in the circulation region). The immobilization region and the circulation region may be defined in any way (for example, on the original images) and they may have any size and position (for example, with the immobilization region outside or overlapping the circulation region, with the circulation region the same as or different from the region of interest).

In an embodiment, the method comprises determining a peak of the comparison values. However, the peak may be of any type (for example, an absolute minimum in negative form) and it may be determined in any way (for example, analytically).

In an embodiment, the method comprises setting the amplitude threshold according to the peak of the comparison values. However, the amplitude threshold may be set in any way according to the peak (for example, simply equal to the candidate threshold providing it).

In an embodiment, the method comprises displaying the thresholded image. However, the thresholded image may be displayed (or more generally output) in any form (for example, in the form of a printout) and in any way (for example, alone, with all the values outside the region of interest equal to the reset value, overlaid on a corresponding original image or fundamental B-mode image). In any case, the thresholded image may also be used in a different way (for example, for calculating and outputting a quantification of the immobilized contrast agent in a region of interest).

In an embodiment, said step of providing at least one filtered image comprises providing a plurality of original images (corresponding to successive acquisition instants during an analysis period of the body-part after the administration of the contrast agent) each one comprising a plurality of original values corresponding to the filtered values; each original value is indicative of a response to an interrogation signal of the corresponding location. However, the original images may be provided in any way, even without acquiring them locally (for example, when the original images are received from another device). The original images may be in any number and acquired with any frequency, based on any type of interrogation signal (for example, magnetic pulses); moreover, the original images may be of any type (for example, in fundamental B-mode) and they may have been acquired in any way (for example, pre-processing them to compensate motion artifacts or to subtract a background image).

In an embodiment, said step of providing at least one filtered image comprises generating the filtered image from at least part of the original images by substantially reducing the contribution of the circulating contrast agent. However, the filtered image may be generated from any number of original images (up to all of them) in any way (for example, with differential targeted enhancement techniques).

In an embodiment, said step of providing a plurality of candidate thresholds comprises calculating a base threshold according to at least part of the original values of said at least part of the original images. However, the base threshold may be calculated in any way (for example, always according to all the original images or according to the filtered image).

In an embodiment, said step of providing a plurality of candidate thresholds comprises calculating the candidate thresholds according to the base threshold. However, the candidate thresholds may be calculated in any other way (for example, directly from the original images without calculating any base threshold).

In an embodiment, the body-part comprises a tissue; said step of providing at least one filtered image comprises processing the original images to substantially reduce a contribution of the tissue before said step of generating the filtered image. However, the tissue may be of any type (see above); moreover, the contribution of the tissue may be reduced at any level (for example, by at least 50-90%) and in any way (for example, in HI, PI, MP mode), down to omit this operation at all.

In an embodiment, said step of generating the filtered image comprises setting each filtered value to one of the original values, which is indicative of a lowest one of the responses to the interrogation signal of the corresponding location in a filtering set of the original images, consisting of one of the original images corresponding to the filtered image and at least one of the original images preceding the original image corresponding to the filtered image. However, the lowest response to the interrogation signal may be determined in any way (for example, based on weighted averages of the original values, corresponding to the maximum in negative form); moreover, the filtering set may comprise any number of original images selected in any way (for example, temporally sub-sampled).

In an embodiment, said step of calculating the candidate thresholds comprises setting the candidate thresholds to corresponding percentages of the base threshold. However, the candidate thresholds may be set according to the base threshold in any way (for example, according to any linear or non-linear function).

In an embodiment, said percentages are distributed uniformly from 0-50% to 150-250%. However, the percentages may be distributed over different ranges (for example, configurable according to the imaging conditions) and in any way (for example, with a pitch increasing moving away from the base threshold).

In an embodiment, said step of calculating a base threshold comprises setting the base threshold according to the original values in the circulation region of said at least part of the original images. However, the base threshold may be set according to any portion of the original images (up to their entirety).

In an embodiment, said step of calculating a base threshold comprises setting the base threshold according to a median of the original values in the circulation region of each one of said at least part of the original images. However, the base threshold may be set according to these median values in any way (for example, by calculating their median again), or more generally according to any other combination of (equal or different) central-tendency statistical parameters (for example, mode, mean, median).

In an embodiment, said step of calculating a plurality of comparison values comprises (for each candidate image) calculating a consolidated immobilization value according to the candidate values in the immobilization region. However, the candidate values in the immobilization region of each candidate image may be consolidated in any type and number of consolidated immobilization values (for example, by combining different statistical parameters).

In an embodiment, said step of calculating a plurality of comparison values comprises (for each candidate image) calculating a consolidated circulation value according to the candidate values in the circulation region. However, the candidate values in the circulation region of each candidate image may be consolidated in any type and number of consolidated circulation values (either the same or different with respect to the consolidated immobilization values).

In an embodiment, said step of calculating a plurality of comparison values comprises (for each candidate image) calculating the comparison value according to a comparison between the consolidated immobilization value and the consolidated circulation value. However, this comparison may be performed in any way (for example, by comparing multiple pairs of consolidated immobilization and circulation values and then aggregating the corresponding results).

In an embodiment, said step of calculating a plurality of comparison values comprises (for each candidate image) setting the consolidated immobilization value to a mean of the candidate values in the immobilization region. However, the mean may be of any type (for example, arithmetic, geometric, harmonic, truncated, midrange) or it may be replaced by a different central-tendency statistical parameter (for example, mode, median).

In an embodiment, said step of calculating a plurality of comparison values comprises (for each candidate image) setting the consolidated circulation value to a mean of the candidate values in the circulation region. However, the mean may be of any type or it may be replaced by a different central-tendency statistical parameter (either the same or different with respect to the consolidated immobilization values).

In an embodiment, said step of calculating a plurality of comparison values comprises (for each candidate image) setting the comparison value to a difference between the consolidated immobilization value and the consolidated circulation value. However, the comparison value may be set in any other way (for example, to a ratio of the consolidated immobilization value and the consolidated circulation value).

In an embodiment, said step of calculating a plurality of comparison values comprises (before said step of calculating the comparison value) normalizing the consolidated immobilization values to the consolidated immobilization value corresponding to a bound value of the candidate thresholds. However, the consolidated immobilization values may be normalized in any way (for example, by dividing them) and to any immobilization offset either depending thereon or not (for example, equal to the mean of the consolidated immobilization values), down to omit this operation at all.

In an embodiment, said step of calculating a plurality of comparison values comprises (before said step of calculating the comparison value) normalizing the consolidated circulation values to the consolidated circulation value corresponding to the bound value of the candidate thresholds.

However, the consolidated circulation values may be normalized in any way and to any circulation offset (either the same or different with respect to the consolidated immobilization values), down to omit this operation at all.

In an embodiment, said step of calculating a plurality of comparison values comprises smoothing the comparison values before said step of determining a peak. However, the comparison values may be smoothed in any way (for example, by applying a Maximum Intensity Projection (MIP) algorithm up to the detection of the peak), down to omit this operation at all.

In an embodiment, said step of setting the amplitude threshold comprises determining the amplitude threshold for providing a percentage of a peak value of the comparison values with a thresholding level higher than the thresholding level of a peak threshold of the candidate thresholds providing the peak value. However, the amplitude threshold may be determined in any other way, even directly according to the peak threshold (for example, by setting the amplitude threshold to a percentage thereof).

In an embodiment, said percentage of the peak value is 40-60% of the peak value. However, the use of different percentages is not excluded in specific imaging conditions.

In an embodiment, said step of setting the amplitude threshold comprises setting the amplitude threshold to the candidate threshold higher than the peak threshold and providing the comparison value being closest to the percentage of the peak value. However, the amplitude threshold may be set to any other value, even not corresponding to one of the candidate thresholds (for example, by interpolation techniques).

Generally, similar considerations apply if the same solution is implemented with an equivalent method (by using similar steps with the same functions of more steps or portions thereof, removing some steps being non-essential, or adding further optional steps); moreover, the steps may be performed in a different order, concurrently or in an interleaved way (at least in part).

An embodiment provides a computer program configured for causing a computing system to perform the above-described method when the computer program is executed on the computing system. An embodiment provides a computer program product comprising a computer readable storage medium embodying a computer program, the computer program being loadable into a working memory of a computing system thereby configuring the computing system to perform the same method. However, the program may be implemented as a stand-alone module, as a plug-in for a pre-existing program (for example, a control program of the ultrasound scanner) or even directly in the latter; in any case, it is also possible to deploy the same solution as a service that is accessed through a network (for example, in the Internet).

Generally, similar considerations apply if the program is structured in a different way, or if additional modules or functions are provided; likewise, the memory structures may be of other types, or may be replaced with equivalent entities (not necessarily consisting of physical storage media). The program may take any form suitable to be used by any computing (or data-processing, instruction execution) system or in connection therewith (for example, within a virtual machine), thereby configuring the computing system to perform the desired operations; particularly, the program may be in the form of external or resident software, firmware, or microcode (either in object code or in source code, for example, to be compiled or interpreted). Moreover, it is possible to provide the program on any computer readable storage medium. The storage medium is any tangible medium (different from transitory signals per se) that may retain and store instructions for use by the computing system. For example, the storage medium may be of the electronic, magnetic, optical, electromagnetic, infrared, or semiconductor type; examples of such storage medium are fixed disks (where the program may be pre-loaded), removable disks, tapes, cards, and the like. The program may be downloaded to the computing system from the storage medium or via a network (for example, the Internet, a wide area network and/or a local area network comprising transmission cables, optical fibers, wireless connections, network devices); one or more network adapters in the computing system receive the program from the network and forwards it for storage in one or more storage devices of the computing system. In any case, the solution according to an embodiment of the present disclosure lends itself to be implemented even with a hardware structure (for example, integrated in one or more chips of semiconductor material), or with a combination of software and hardware suitably programmed or otherwise configured.

An embodiment provides a system comprising means configured for performing the steps of the above-mentioned method. An embodiment provides a system comprising a circuitry (i.e., any hardware suitably configured, for example, by software) for performing each step of the same method. However, the system may be of any type (for example, a different diagnostic imaging system such as based on Magnetic Resonance Imaging (MRI) or X-ray Computed Tomography (CT)). Alternatively, the same solution may be applied in a system comprising an acquisition device (such as the ultrasound scanner) and a distinct (general purpose) computing machine; in this case, the information (for example, the filtered image or the original images) is transferred from the acquisition device to the computing machine for its processing (for example, through a removable storage unit or a digital, analogue or network connection). In any case, the system may have any other architecture (for example, of client/server type) and it may comprise similar elements (such as cache memories temporarily storing the programs or parts thereof).

Generally, similar considerations apply if the system has a different structure or comprises equivalent components, or it has other operative characteristics. In any case, every component thereof may be separated into more elements, or two or more components may be combined together into a single element; moreover, each component may be replicated to support the execution of the corresponding operations in parallel. In any case, unless specified otherwise, any interaction between different components generally does not need to be continuous, and it may be either direct or indirect through one or more intermediaries.

An embodiment provides a diagnostic method for analyzing a body-part of a patient, the method comprising administering a contrast agent to the patient to cause the body-part to be perfused with the contrast agent, the contrast agent being capable of circulating within the patient and of being substantially immobilized on a biological target, acquiring said at least one filtered image, the filtered image being processed according to the above-mentioned method to obtain the corresponding thresholded image, and evaluating a condition of the body-part according to the thresholded image. However, the same method may find application in any kind of diagnostic applications (in the broadest meaning of the term, for example, aimed at either discovering new lesions or monitoring known lesions) and for analyzing any kind of body-part (for example, organs, such as liver, prostate or heart, regions or tissues) of any (human or animal) patient.

The invention claimed is:

1. A method for analyzing a body-part of a patient, the body-part having been perfused before performing the method with a contrast agent capable of circulating within the patient and of being substantially immobilized on a biological target, wherein the method comprises:
   providing at least one filtered image comprising a plurality of filtered values for corresponding locations of the body-part, each filtered value comprising an indication of the immobilized contrast agent at the corresponding location with a contribution of the circulating contrast agent being substantially reduced,
   generating a thresholded image comprising a plurality of thresholded values corresponding to the filtered values, the thresholded image being generated by setting each thresholded value to the corresponding filtered value or to a reset value according to a comparison of the filtered value with an amplitude threshold,
   providing a plurality of candidate thresholds defined by corresponding candidate values of the amplitude threshold,
   generating a plurality of candidate images corresponding to the candidate thresholds each one comprising a plurality of candidate values corresponding to the filtered values, each candidate image being generated by setting each candidate value to the corresponding filtered value or to the reset value according to said comparison of the filtered value with the candidate threshold,
   calculating a plurality of comparison values corresponding to the candidate images, the comparison value of each candidate image being calculated according to a further comparison between the candidate values in an immobilization region corresponding to a group of locations containing a significant amount of the immobilized contrast agent and the candidate values in a circulation region corresponding to at least part of the locations excluding the immobilization region,
   determining a peak of the comparison values, and
   setting the amplitude threshold according to the peak of the comparison values.

2. The method according to claim 1, wherein the method comprises:
   displaying the thresholded image.

3. The method according to claim 1, wherein said providing at least one filtered image comprises:
   providing a plurality of original images, corresponding to successive acquisition instants during an analysis period of the body-part after the administration of the contrast agent, each one comprising a plurality of original values corresponding to the filtered values, each original value being indicative of a response to an interrogation signal of the corresponding location, and
   generating the filtered image from at least part of the original images by substantially reducing the contribution of the circulating contrast agent, and wherein said providing a plurality of candidate thresholds comprises:
   calculating a base threshold according to at least part of the original values of said at least part of the original images, and
   calculating the candidate thresholds according to the base threshold.

4. The method according to claim 3, wherein the body-part comprises a tissue, said providing at least one filtered image comprising:
   processing the original images to substantially reduce a contribution of the tissue before said generating the filtered image.

5. The method according to claim 3, wherein said generating the filtered image comprises:
   setting each filtered value to one of the original values indicative of a lowest one of the responses to the interrogation signal of the corresponding location in a filtering set of the original images consisting of one of the original images corresponding to the filtered image and at least one of the original images preceding the original image corresponding to the filtered image.

6. The method according to claim 3, wherein said calculating the candidate thresholds comprises:
   setting the candidate thresholds to corresponding percentages of the base threshold.

7. The method according to claim 6, wherein said percentages are distributed uniformly from 0-50% to 150-250%.

8. The method according to claim 3, wherein said calculating a base threshold comprises:
   setting the base threshold according to the original values in the circulation region of said at least part of the original images.

9. The method according to claim 8, wherein said calculating a base threshold comprises:
   setting the base threshold according to a median of the original values in the circulation region of each one of said at least part of the original images.

10. The method according to claim 1, wherein said calculating a plurality of comparison values comprises, for each candidate image:
    calculating a consolidated immobilization value according to the candidate values in the immobilization region,
    calculating a consolidated circulation value according to the candidate values in the circulation region, and
    calculating the comparison value according to a comparison between the consolidated immobilization value and the consolidated circulation value.

11. The method according to claim 10, wherein said calculating a plurality of comparison values comprises, for each candidate image:
    setting the consolidated immobilization value to a mean of the candidate values in the immobilization region,
    setting the consolidated circulation value to a mean of the candidate values in the circulation region, and
    setting the comparison value to a difference between the consolidated immobilization value and the consolidated circulation value.

12. The method according to claim 10, wherein said calculating a plurality of comparison values comprises, before said calculating the comparison value:
    normalizing the consolidated immobilization values to the consolidated immobilization value corresponding to a bound value of the candidate thresholds, and
    normalizing the consolidated circulation values to the consolidated circulation value corresponding to the bound value of the candidate thresholds.

13. The method according to claim 1, wherein said calculating a plurality of comparison values comprises:
    smoothing the comparison values before said determining a peak.

14. The method according to claim 1, wherein said setting the amplitude threshold comprises:
   determining the amplitude threshold for providing a percentage of a peak value of the comparison values with a thresholding level higher than the thresholding level of a peak threshold of the candidate thresholds providing the peak value.

15. The method according to claim 14, wherein said percentage of the peak value is 40-60% of the peak value.

16. The method according to claim 14, wherein said setting the amplitude threshold comprises:
   setting the amplitude threshold to the candidate threshold higher than the peak threshold and providing the comparison value being closest to the percentage of the peak value.

17. A non-transitory computer-readable medium storing a computer program configured for causing a computing system to perform a method for analyzing a body-part of a patient when the computer program is executed on the computing system, the body-part having been perfused before performing the method with a contrast agent capable of circulating within the patient and of being substantially immobilized on a biological target, wherein the method comprises:
   providing at least one filtered image comprising a plurality of filtered values for corresponding locations of the body-part, each filtered value comprising an indication of the immobilized contrast agent at the corresponding location with a contribution of the circulating contrast agent being substantially reduced,
   generating a thresholded image comprising a plurality of thresholded values corresponding to the filtered values, the thresholded image being generated by setting each thresholded value to the corresponding filtered value or to a reset value according to a comparison of the filtered value with an amplitude threshold,
   providing a plurality of candidate thresholds defined by corresponding candidate values of the amplitude threshold,
   generating a plurality of candidate images corresponding to the candidate thresholds each one comprising a plurality of candidate values corresponding to the filtered values, each candidate image being generated by setting each candidate value to the corresponding filtered value or to the reset value according to said comparison of the filtered value with the candidate threshold,
   calculating a plurality of comparison values corresponding to the candidate images, the comparison value of each candidate image being calculated according to a further comparison between the candidate values in an immobilization region corresponding to a group of locations containing a significant amount of the immobilized contrast agent and the candidate values in a circulation region corresponding to at least part of the locations excluding the immobilization region,
   determining a peak of the comparison values, and
   setting the amplitude threshold according to the peak of the comparison values.

18. A computer program product comprising a computer readable storage medium embodying a computer program, the computer program being loadable into a working memory of a computing system thereby configuring the computing system to perform a method for analyzing a body-part of a patient, the body-part having been perfused before performing the method with a contrast agent capable of circulating within the patient and of being substantially immobilized on a biological target, wherein the method comprises:
   providing at least one filtered image comprising a plurality of filtered values for corresponding locations of the body-part, each filtered value comprising an indication of the immobilized contrast agent at the corresponding location with a contribution of the circulating contrast agent being substantially reduced,
   generating a thresholded image comprising a plurality of thresholded values corresponding to the filtered values, the thresholded image being generated by setting each thresholded value to the corresponding filtered value or to a reset value according to a comparison of the filtered value with an amplitude threshold,
   providing a plurality of candidate thresholds defined by corresponding candidate values of the amplitude threshold,
   generating a plurality of candidate images corresponding to the candidate thresholds each one comprising a plurality of candidate values corresponding to the filtered values, each candidate image being generated by setting each candidate value to the corresponding filtered value or to the reset value according to said comparison of the filtered value with the candidate threshold,
   calculating a plurality of comparison values corresponding to the candidate images, the comparison value of each candidate image being calculated according to a further comparison between the candidate values in an immobilization region corresponding to a group of locations containing a significant amount of the immobilized contrast agent and the candidate values in a circulation region corresponding to at least part of the locations excluding the immobilization region,
   determining a peak of the comparison values, and setting the amplitude threshold according to the peak of the comparison values.

19. A system comprising means configured for performing the steps of a method for analyzing a body-part of a patient, the body-part having been perfused before performing the method with a contrast agent capable of circulating within the patient and of being substantially immobilized on a biological target, wherein the method comprises:
   providing at least one filtered image comprising a plurality of filtered values for corresponding locations of the body-part, each filtered value comprising an indication of the immobilized contrast agent at the corresponding location with a contribution of the circulating contrast agent being substantially reduced,
   generating a thresholded image comprising a plurality of thresholded values corresponding to the filtered values, the thresholded image being generated by setting each thresholded value to the corresponding filtered value or to a reset value according to a comparison of the filtered value with an amplitude threshold,
   providing a plurality of candidate thresholds defined by corresponding candidate values of the amplitude threshold,
   generating a plurality of candidate images corresponding to the candidate thresholds each one comprising a plurality of candidate values corresponding to the filtered values, each candidate image being generated by setting each candidate value to the corresponding filtered value or to the reset value according to said comparison of the filtered value with the candidate threshold, calculating a plurality of comparison values corresponding to the candidate images, the comparison value of each candidate image being calculated according to a further comparison between the candidate values in an immobilization region corresponding to a group of locations containing a significant amount of the immobilized contrast agent and the candidate values in a circulation region corresponding to at least part of the locations excluding the immobilization region, determining a peak of the comparison values, and setting the amplitude threshold according to the peak of the comparison values.

20. A system comprising a circuitry for performing each step of a method for analyzing a body-part of a patient, the body-part having been perfused before performing the method with a contrast agent capable of circulating within the patient and of being substantially immobilized on a biological target, wherein the method comprises:

providing at least one filtered image comprising a plurality of filtered values for corresponding locations of the body-part, each filtered value comprising an indication of the immobilized contrast agent at the corresponding location with a contribution of the circulating contrast agent being substantially reduced, generating a thresholded image comprising a plurality of thresholded values corresponding to the filtered values, the thresholded image being generated by setting each thresholded value to the corresponding filtered value or to a reset value according to a comparison of the filtered value with an amplitude threshold, providing a plurality of candidate thresholds defined by corresponding candidate values of the amplitude threshold, generating a plurality of candidate images corresponding to the candidate thresholds each one comprising a plurality of candidate values corresponding to the filtered values, each candidate image being generated by setting each candidate value to the corresponding filtered value or to the reset value according to said comparison of the filtered value with the candidate threshold, calculating a plurality of comparison values corresponding to the candidate images, the comparison value of each candidate image being calculated according to a further comparison between the candidate values in an immobilization region corresponding to a group of locations containing a significant amount of the immobilized contrast agent and the candidate values in a circulation region corresponding to at least part of the locations excluding the immobilization region, determining a peak of the comparison values, and setting the amplitude threshold according to the peak of the comparison values.

21. A diagnostic method for analyzing a body-part of a patient, the diagnostic method comprising:

administering a contrast agent to the patient to cause the body-part to be perfused with the contrast agent, the contrast agent being capable of circulating within the patient and of being substantially immobilized on a biological target, acquiring at least one filtered image comprising a plurality of filtered values for corresponding locations of the body-part, each filtered value comprising an indication of the immobilized contrast agent at the corresponding location with a contribution of the circulating contrast agent being substantially reduced, the filtered image being processed according to the method of claim 1 to obtain the corresponding thresholded image, and evaluating a condition of the body-part according to the thresholded image.

* * * * *